US012234262B1

(12) United States Patent
Sohn et al.

(10) Patent No.: US 12,234,262 B1
(45) Date of Patent: Feb. 25, 2025

(54) VACCINIA VIRUS RECOMBINANT A33R PROTEIN AND KIT FOR DIAGNOSING ANTIBODIES AGAINST ORTHOPOXVIRUS COMPRISING THE SAME

(71) Applicant: REPUBLIC OF KOREA (DEFENSE ACQUISITION PROGRAM ADMINISTRATION), Gwacheon-si (KR)

(72) Inventors: Eun-Ju Sohn, Pohang-si (KR); Hyangju Kang, Pohang-si (KR); So Yun Park, Jung-gu (KR)

(73) Assignee: REPUBLIC OF KOREA (DEFENSE ACQUISITION PROGRAM ADMINISTRATION), Gwacheon-si (KR)

( * ) Notice: Subject to any disclaimer, the term of this patent is extended or adjusted under 35 U.S.C. 154(b) by 0 days.

(21) Appl. No.: 18/393,436

(22) Filed: Dec. 21, 2023

(30) Foreign Application Priority Data

Oct. 17, 2023 (KR) .................. 10-2023-0138774

(51) Int. Cl.
C07K 14/005 (2006.01)
C12N 15/82 (2006.01)
G01N 33/569 (2006.01)

(52) U.S. Cl.
CPC ............ *C07K 14/005* (2013.01); *C12N 15/82* (2013.01); *G01N 33/56983* (2013.01); *C07K 2319/04* (2013.01); *C07K 2319/21* (2013.01)

(58) Field of Classification Search
None
See application file for complete search history.

(56) References Cited

U.S. PATENT DOCUMENTS 4,940,838 A 7/1990 Schilperoort et al.
2013/0295065 A1 11/2013 Shulman et al.

FOREIGN PATENT DOCUMENTS

| EP | 0 116 718 B1 | 8/1984 |
| EP | 0 120 516 B1 | 10/1984 |
| WO | WO-2009/158716 A1 | 12/2009 |

OTHER PUBLICATIONS

Smallpox and Related Orthopoxviruses in Medical Aspects of Biological Warfare, Goff et al., pp. 615-644, 2018 (Year: 2018).*
Ahmed, Syed Faraz et al., Vaccinia-Virus-Based Vaccines Are Expected to Elicit Highly Cross-Reactive Immunity to the 2022 Monkeypox Virus, Viruses, 2022, 14, 1960, 11 pages.
Altschul et al., "Basic Local Alignment Search Tool," J. Mol. Biol. vol. 215, pp. 403-410, 1990.

(Continued)

*Primary Examiner* — Karl J Puttlitz
(74) *Attorney, Agent, or Firm* — Foley & Lardner LLP

(57) ABSTRACT

The present invention relates to a vaccinia virus recombinant A33R protein and a kit for diagnosing antibodies against orthopoxvirus containing the same, and more particularly, to a recombinant A33R protein in which the transmembrane domain of the vaccinia virus A33R protein is replaced with a peptide linker, a recombinant vector for efficiently expressing the recombinant A33R protein, a transgenic organism, a method for producing the recombinant A33R protein, a composition and kit for diagnosing antibodies against orthopoxvirus containing the recombinant A33R protein.

16 Claims, 11 Drawing Sheets

Specification includes a Sequence Listing.

(56) References Cited

OTHER PUBLICATIONS

D.J. Lipman et al., "Rapid and Sensitive Protein Similarity Searches", Science, Mar. 22, 1985, pp. 1435-1441, vol. 227.
Pearson & Lipman, "Improved tools for biological sequence comparison," Proc. Natl. Acad. Sci, vol. 85, pp. 2444-2448, Apr. 1988.

* cited by examiner

FIG. 1

(A) | MacTp | NB | A33RdN1(58-185) | L10H | DEL | RD29Bt |

(B) | MacTp | NB | A33RdN2(82-185) | L10H | DEL | RD29Bt |

(C) | MacTp | NB | A33RdTM | L10H | RD29Bt |

(D) | MacTp | A33RdTM | L10H | RD29Bt |

(E) | MacTp | NB | A33RdTM | aghFc | RD29Bt |

FIG. 7 pTEX-A33RdTMxL10H

| XbaI | BamHI | XmaI | XhoI |
|------|-------|------|------|
|      | A33RdTM |  L10H |     |

ATGACACCAGAAGACGAGAAAACGAGCAGACATCGTGTTCTCGGCTACGTTACTGGTTACGGAGACAAAATTCAGGGAGACAAAATCAGGGAAAGAATAAACGCAAACGCTGA
TT............GTGCGCCTAAATCAATGCATGTCTGCTAACGAGGCTGTATTACTGACGCCGTCGTGTGCGTTGCCGTTGCCATCATCATCACTACTA
TAGAAAGGTTGCGTCAGCACTACACAGCAATTCACAAAGAAAGCTGTAATGGTTTATATTACAAATCGATGTCTCTTGATTACCAGACTACCA
GTTATTCTGGGATGCTAAAGCTAAGCAATTGCACTGCGGAATCATCGCCAATAAATCGATGTCTCTTGATTACCTGGTCATTGATTATGTTGAGG
ATACATGGGGATCTGATTGGTATCAAAAATCATCGATTATCAAGATTTCGATGTATCCAAGAAGTATTTGTTTAAA
CAATGAAC ccgcaccatcaccaccatcaccactag nggcg (SEQ ID NO: 28)

mg mmtpendeeqtsvfsahvgdkiaglnhtkroi ss vrtngcmsaneaaitdaavavaassthrkvassttqvdheesnglypqgscvhsdygtfsdaknctaesstlp
nksdvltwildyvedtwgsdqmpitkttsdyqdisdvsqgevtkyfcvktmqpr hhhhhhhmi (SEQ ID NO: 22)

SEQUENCE LISTING

```
Sequence total quantity: 30
SEQ ID NO: 1            moltype = AA  length = 185
FEATURE                 Location/Qualifiers
source                  1..185
                        mol_type = protein
                        organism = Vaccinia virus
SEQUENCE: 1
MMTPENDEEQ TSVFSATVYG DKIQGKNKRK RVIGLCIRIS MVISLLSMIT MSAFLIVRLN    60
QCMSANEAAI TDAAVAVAAA SSTHRKVASS TTQYDHKESC NGLYYQGSCY ILHSDYQLFS   120
DAKANCTAES STLPNKSDVL ITWLIDYVED TWGSDGNPIT KTTSDYQDSD VSQEVRKYFC   180
VKTMN                                                              185

SEQ ID NO: 2            moltype = AA  length = 167
FEATURE                 Location/Qualifiers
source                  1..167
                        mol_type = protein
                        organism = synthetic construct
SEQUENCE: 2
MMTPENDEEQ TSVFSATVYG DKIQGKNKRK RVIGGGGSVR LNQCMSANEA AITDAAVAVA    60
AASSTHRKVA SSTTQYDHKE SCNGLYYQGS CYILHSDYQL FSDAKANCTA ESSTLPNKSD   120
VLITWLIDYV EDTWGSDGNP ITKTTSDYQD SDVSQEVRKY FCVKTMN                 167

SEQ ID NO: 3            moltype = DNA  length = 501
FEATURE                 Location/Qualifiers
source                  1..501
                        mol_type = other DNA
                        organism = synthetic construct
SEQUENCE: 3
atgatgactc ctgagaatga tgaagaacaa acatctgttt tctccgccac ggtttatgga    60
gataaaattc aaggaaagaa caaaagaaaa cgagtaatag gcggggggtgg gtcagtcaga   120
ctaaaccagt gcatgtctgc aaatgaagcg gcaataactg atgctgctgt tgcctagct   180
gcagcttcca gcactcatag gaaagtggca tcatctacca cacagtatga tcataaggag   240
agttgcaatg gtttgtacta tcaaggttct tgttatattc ttcactcgga ctaccagctc   300
ttttcagacg caaaagctaa ttgtactgct gagagcagca cactgcccaa caagtctgat   360
gttcttatca cttggttaat tgactatgtt gaagatacat ggggatcaga tggaaatcca   420
atcacaaaga ctaccagtga ctaccaagat agtgatgtgt cacaagaagt ccgtaagtat   480
ttttgtgtga aaacaatgaa t                                           501
```

```
SEQ ID NO: 4          moltype = AA   length = 5
FEATURE               Location/Qualifiers
source                1..5
                      mol_type = protein
                      note = Amino acid residues at the positions 1 to 5 are
                       repeated 1 to 5 times.
                      organism = synthetic construct
REPEAT                1
REPEAT                2
REPEAT                3
REPEAT                4
REPEAT                5
SEQUENCE: 4
GGGGS                                                                     5

SEQ ID NO: 5          moltype = DNA  length = 250
FEATURE               Location/Qualifiers
source                1..250
                      mol_type = other DNA
                      organism = synthetic construct
SEQUENCE: 5
atggctcgct cgtttggagc taacagtacc gttgtgttgg cgatcatctt cttcggtgag          60
tgattttccg atcttcttct ccgatttaga tctcctctac attgttgctt aatctcagaa         120
ccttttttcg ttgttcctgg atctgaatgt gtttgtttgc aatttcacga tcttaaaagg         180
ttagatctcg attggtattg acgattggaa tctttacgat ttcaggatgt tatttgcgtt         240
gtcctctgca                                                               250

SEQ ID NO: 6          moltype = AA   length = 4
FEATURE               Location/Qualifiers
source                1..4
                      mol_type = protein
                      organism = synthetic construct
SEQUENCE: 6
HDEL                                                                      4

SEQ ID NO: 7          moltype = AA   length = 4
FEATURE               Location/Qualifiers
source                1..4
                      mol_type = protein
                      organism = synthetic construct
SEQUENCE: 7
HEEL                                                                      4

SEQ ID NO: 8          moltype = AA   length = 4
FEATURE               Location/Qualifiers
source                1..4
                      mol_type = protein
                      organism = synthetic construct
SEQUENCE: 8
KDEL                                                                      4

SEQ ID NO: 9          moltype = AA   length = 4
FEATURE               Location/Qualifiers
source                1..4
                      mol_type = protein
                      organism = synthetic construct
SEQUENCE: 9
KEEL                                                                      4

SEQ ID NO: 10         moltype = AA   length = 4
FEATURE               Location/Qualifiers
source                1..4
                      mol_type = protein
                      organism = synthetic construct
SEQUENCE: 10
RDEL                                                                      4

SEQ ID NO: 11         moltype = AA   length = 4
FEATURE               Location/Qualifiers
source                1..4
                      mol_type = protein
                      organism = synthetic construct
SEQUENCE: 11
REEL                                                                      4

SEQ ID NO: 12         moltype = AA   length = 10
FEATURE               Location/Qualifiers
source                1..10
```

```
                    mol_type = protein
                    organism = synthetic construct
SEQUENCE: 12
HHHHHHHHHH                                                              10

SEQ ID NO: 13       moltype = DNA  length = 853
FEATURE             Location/Qualifiers
source              1..853
                    mol_type = other DNA
                    organism = synthetic construct
SEQUENCE: 13
tctagaatta ttacatcaaa acaaaaaatg gctcgctcgt ttggagctaa cagtaccgtt        60
gtgttggcga tcatcttctt cggtgagtga ttttccgatc ttcttctccg atttagatct       120
cctctacatt gttgcttaat ctcagaacct ttttcgattc ttcctggatc tgaatgtgtt       180
tgtttgcaat ttcacgatct taaaaggtta gatctcgatt ggtattgacg attggaatct       240
ttacgatttc aggatgttat ttgcgttgtc ctctgcagga tccatgatga ctcctgagaa       300
tgatgaagaa caaacatctg ttttctccgc cacggtttat ggagataaaa ttcaaggaaa       360
gaacaaaaga aaacgagtaa taggcggggg tgggtcagtc agactaaacc agtgcatgtc       420
tgcaaatgaa gcggcaataa ctgatgctgc tgttgccgta gctgcagctt ccagcactca       480
taggaaagtg gcatcatcta ccacacagta tgatcataag gagagttgca atggtttgta       540
ctatcaaggt tcttgttata ttcttcactc ggactaccag ctcttttcag acgcaaaagc       600
taattgtact gctgagagca gcacactgcc caacaagtct gatgttctta tcacttggtt       660
aattgactat gttgaagata catggggatc agatggaaat ccaatcacaa agactaccag       720
tgactaccaa gatagtgatg tgtcacaaga agtccgtaag tatttttgtg tgaaaacaat       780
gaatccccgg ggtgggggag gcagtcacca ccatcaccac catcaccacc accatgatga       840
gctctagctc gag                                                         853

SEQ ID NO: 14       moltype = AA  length = 189
FEATURE             Location/Qualifiers
source              1..189
                    mol_type = protein
                    organism = synthetic construct
SEQUENCE: 14
GSMMTPENDE EQTSVFSATV YGDKIQGKNK RKRVIGGGGS VRLNQCMSAN EAAITDAAVA        60
VAAASSTHRK VASSTTQYDH KESCNGLYYQ GSCYILHSDY QLFSDAKANC TAESSTLPNK       120
SDVLITWLID YVEDTWGSDG NPITKTTSDY QDSDVSQEVR KYFCVKTMNP RGGGGSHHHH       180
HHHHHHDEL                                                              189

SEQ ID NO: 15       moltype = DNA  length = 737
FEATURE             Location/Qualifiers
source              1..737
                    mol_type = other DNA
                    organism = synthetic construct
SEQUENCE: 15
tctagaatta ttacatcaaa acaaaaaatg gctcgctcgt ttggagctaa cagtaccgtt        60
gtgttggcga tcatcttctt cggtgagtga ttttccgatc ttcttctccg atttagatct       120
cctctacatt gttgcttaat ctcagaacct ttttcgttg ttcctggatc tgaatgtgtt       180
tgtttgcaat ttcacgatct taaaaggtta gatctcgatt ggtattgacg attggaatct       240
ttacgatttc aggatgttta tttgcgttgt cctctgcagg atcccgccta atcaatgca        300
tgtctgctaa cgaggctgct attactgacg ccgctgttgc cgttgctgct gcatcatcta       360
ctcatagaaa ggttgcgtct agcactacac aatatgatca caaagaaagc tgtaatgcgt       420
tatattacca gggttcttgt tatatattac attcagacta ccagttattc tcggatgcta       480
aagcaaattg cactgcggaa tcatcaacac tacccaataa atccgatgtc ttgattacct       540
ggctcattga ttatgttgag gatacatggg gatctgatgg taatccaatt acaaaaacta       600
catccgatta tcaagattct gatgtatcac aagaagttag aaagtatttt tgtgttaaaa       660
caatgaaccc ccggggtggg ggaggcagtc accaccatca ccaccatcac caccaccatg       720
atgagctcta gctcgag                                                     737

SEQ ID NO: 16       moltype = AA  length = 150
FEATURE             Location/Qualifiers
source              1..150
                    mol_type = protein
                    organism = synthetic construct
SEQUENCE: 16
GSRLNQCMSA NEAAITDAAV AVAAASSTHR KVASSTTQYD HKESCNGLYY QGSCYILHSD        60
YQLFSDAKAN CTAESSTLPN KSDVLITWLI DYVEDTWGSD GNPITKTTSD YQDSDVSQEV       120
RKYFCVKTMN PRGGGGSHHH HHHHHHHDEL                                        150

SEQ ID NO: 17       moltype = DNA  length = 665
FEATURE             Location/Qualifiers
source              1..665
                    mol_type = other DNA
                    organism = synthetic construct
SEQUENCE: 17
tctagaatta ttacatcaaa acaaaaaatg gctcgctcgt ttggagctaa cagtaccgtt        60
gtgttggcga tcatcttctt cggtgagtga ttttccgatc ttcttctccg atttagatct       120
cctctacatt gttgcttaat ctcagaacct ttttcgttg ttcctggatc tgaatgtgtt       180
tgtttgcaat ttcacgatct taaaaggtta gatctcgatt ggtattgacg attggaatct       240
ttacgatttc aggatgttta tttgcgttgt cctctgcagg atcctctact catagaaagg       300
```

```
ttgcgtctag cactacacaa tatgatcaca agaaagctg taatggttta tattaccagg    360
gttcttgtta tatattacat tcagactacc agttattctc ggatgctaaa gcaaattgca    420
ctgcggaatc atcaacacta cccaataaat ccgatgtctt gattacctgg ctcattgatt    480
atgttgagga tacatgggga tctgatggta atccaattac aaaaactaca tccgattatc    540
aagattctga tgtatcacaa gaagttagaa agtattttg tgttaaaaca atgaaccccc    600
ggggtggggg aggcagtcac caccatcacc accatcacca ccaccatgat gagctctagc    660
tcgag                                                                665

SEQ ID NO: 18           moltype = AA  length = 126
FEATURE                 Location/Qualifiers
source                  1..126
                        mol_type = protein
                        organism = synthetic construct
SEQUENCE: 18
GSSTHRKVAS STTQYDHKES CNGLYYQGSC YILHSDYQLF SDAKANCTAE SSTLPNKSDV     60
LITWLIDYVE DTWGSDGNPI TKTTSDYQDS DVSQEVRKYF CVKTMNPRGG GGSHHHHHHH    120
HHHDEL                                                               126

SEQ ID NO: 19           moltype = DNA  length = 825
FEATURE                 Location/Qualifiers
source                  1..825
                        mol_type = other DNA
                        organism = synthetic construct
SEQUENCE: 19
tctagaatta ttcatcaaa acaaaaaatg gcttcctcta tgctctcttc cgctactatg     60
gttgcgtctc cggctcaggc cactatggtc gtcctcctca acggacttaa gtcctccgct    120
gccttcccag ccacccgcaa ggctaacaac gacactactt ccatcacaag caacggcgga    180
agagttaact gcatgcaggt gtggcctccg attggaaaga agaagtttga gactctctct    240
taccttcctg accttaccgg atccatgatg acaccagaaa acgacgaaga gcagacatct    300
gtgttctccg ctactgttta cggagacaaa attcagggaa agaataaacg caaacgcgtg    360
attggaggag ggggttcagt gcgcctaaat caatgcatgt ctgctaacga ggctgctatt    420
actgacgccg ctgttgccgt tgctgctgca tcatctactc atagaaaggt tgcgtctagc    480
actacacaat atgatcacaa agaaagctgt aatggtttat attaccaggg ttcttgttat    540
atattacatt cagactacca gttattctcg gatgctaaag caaattgcac tgcggaatca    600
tcaacactac ccaataaatc cgatgtcttg attacctggc tcattgatta tgttgaggat    660
acatggggat ctgatggtaa tccaattaca aaaactacat ccgattatca agattctgat    720
gtatcacaag aagttagaaa gtattttgt gttaaaacaa tgaaccccg ggtgggga     780
ggcagtcacc accatcacca ccatcaccac ccattagc tcgag                     825

SEQ ID NO: 20           moltype = AA  length = 263
FEATURE                 Location/Qualifiers
source                  1..263
                        mol_type = protein
                        organism = synthetic construct
SEQUENCE: 20
MASSMLSSAT MVASPAQATM VAPFNGLKSS AAFPATRKAN NDTTSITSNG GRVNCMQVWP     60
PIGKKKFETL SYLPDLTGSM MTPENDEEQT SVFSATVYGD KIQGKNKRKR VIGGGGSVRL    120
NQCMSANEAA ITDAAVAVAA ASSTHRKVAS STTQYDHKES CNGLYYQGSC YILHSDYQLF    180
SDAKANCTAE SSTLPNKSDV LITWLIDYVE DTWGSDGNPI TKTTSDYQDS DVSQEVRKYF    240
CVKTMNPRGG GGSHHHHHHH HHH                                            263

SEQ ID NO: 21           moltype = DNA  length = 597
FEATURE                 Location/Qualifiers
source                  1..597
                        mol_type = other DNA
                        organism = synthetic construct
SEQUENCE: 21
tctagaatta ttcatcaaa acaaaaaatg ggatccatga tgacaccaga aaacgacgaa     60
gagcagacat ctgtgttctc cgctactgtt tacggagaca aaattcaggg aaagaataaa    120
cgcaaacgcg tgattggagg agggggttca gtgcgcctaa atcaatgcat gtctgctaac    180
gaggctgcta ttactgacgc cgctgttgcc gttgctgctg catcatctac tcatagaaag    240
gttgcgtcta gcactacaca atatgatcac aaagaaagct gtaatggttt atattaccag    300
ggttcttgtt atatattaca ttcagactac agttattct ggatgctaa agcaaattgc    360
actgcggaat catcaacact acccaataaa tccgatgtct tgattacctg gctcattgat    420
tatgttgagg atacatgggg atctgatggt aatccaatta caaaaactac atccgattat    480
caagattctg atgtatcaca agaagttaga agtatttt gtgttaaaac aatgaaccc    540
cgggtgggg gaggcagtca ccaccatcac caccatcacc accatta gctcgag          597

SEQ ID NO: 22           moltype = AA  length = 187
FEATURE                 Location/Qualifiers
source                  1..187
                        mol_type = protein
                        organism = synthetic construct
SEQUENCE: 22
MGSMMTPEND EEQTSVFSAT VYGDKIQGKN KRKRVIGGGG SVRLNQCMSA NEAAITDAAV     60
AVAAASSTHR KVASSTTQYD HKESCNGLYY QGSCYILHSD YQLFSDAKAN CTAESSTLPN    120
KSDVLITWLI DYVEDTWGSD GNPITKTTSD YQDSDVSQEV RKYFCVKTMN PRGGGGSHHH    180
HHHHHH                                                               187
```

-continued

```
SEQ ID NO: 23            moltype = DNA    length = 1465
FEATURE                  Location/Qualifiers
source                   1..1465
                         mol_type = other DNA
                         organism = synthetic construct
SEQUENCE: 23
tctagaatta ttacatcaaa acaaaaaatg gctcgctcgt ttggagctaa cagtaccgtt    60
gtgttggcga tcatcttctt cggtgagtga ttttccgatc ttcttctccg atttagatct   120
cctctacatt gttgcttaat ctcagaacct tttttcgttg ttcctggatc tgaatgtgtt   180
tgtttgcaat ttcacgatct taaaaggtta gatctcgatt ggtattgacg attgaatct    240
ttacgatttc aggatgttat ttgcgttgtc ctctgcagga tccatgatga caccagaaaa   300
cgacgaagag cagacatctg tgttctccgc tactgtttac ggagacaaaa ttcagggaaa   360
gaataaacgc aaacgcgtga ttggaggagg gggttcagtc cgcctaaatc aatgcatgtc   420
tgctaacgag gctgctatta ctgacgccgc tgttgccgtt gctgctgcat catctactca   480
tagaaaggtt gcgtctagca ctacacaata tgatcacaaa gaaagctgta atggtttata   540
ttaccagggt tcttgttata tattacattc agactaccag ttattctcgg atgctaaagc   600
aaaattgcact gcggaatcat caacactacc caataaatcc gatgtcttga ttacctggct   660
cattgattat gttgaggata catgggggatc tgatggtaat ccaattacaa aaactacatc   720
cgattatcaa gattctgatg tatcacaaga agttagaaag tatttttgtg ttaaaacaat   780
gaaccccgg ggtccacctt gcccagctcc tgaattgctt ggaggtcctt ctgttttctc    840
ttttccacct aagccaaaag atacattgat gatttctagg acacctgagg ttacttgcgt   900
tgttgttgat gtttcacatg aagatccaga ggttaagttt aattggtacg ttgatggagt   960
tgaagttcat aatgctaaga ctaaaccaag ggaagagcaa tacgcctcta catacagagt  1020
tgtttcagtt ttgactgttc ttcatcaaga ttggcttaac ggaaaggaat acaagtgtaa  1080
agtttctaac aaggctttgc cagctcctat cgaaaagaca atttcaaagg ctaaaggtca  1140
accaagggag cctcaagttt acactcttcc accatcagga agaattga caaagaacca   1200
agtttcattg acttgccttg ttaagggatt ctacccttct gatattgctg ttgaatggga  1260
gtcaaacggt caaccagaaa acaactacaa gactacacca cctgttcttg attctgatgg  1320
atctttcttt ctttactcta aacttactgt tgataagtca agatggcaac agggtaatgt  1380
tttctcttgt tcagttatgc acgaggcact tcacaatcac tacacacaaa aatctttatc  1440
tttatcacct ggtaaataac tcgag                                        1465

SEQ ID NO: 24            moltype = AA    length = 393
FEATURE                  Location/Qualifiers
source                   1..393
                         mol_type = protein
                         organism = synthetic construct
SEQUENCE: 24
GSMMTPENDE EQTSVFSATV YGDKIQGKNK RKRVIGGGGS VRLNQCMSAN EAAITDAAVA    60
VAAASSTHRK VASSTTQYDH KESCNGLYYQ GSCYILHSDY QLFSDAKANC TAESSTLPNK   120
SDVLITWLID YVEDTWGSDG NPITKTTSDY QDSDVSQEVR KYFCVKTMNP RGPPCPAPEL   180
LGGPSVFLFP PKPKDTLMIS RTPEVTCVVV DVSHEDPEVK FNWYVDGVEV HNAKTKPREE   240
QYASTYRVVS VLTVLHQDWL NGKEYKCKVS NKALPAPIEK TISKAKGQPR EPQVYTLPPS   300
RDELTKNQVS LTCLVKGFYP SDIAVEWESN GQPENNYKTT PPVLDSDGSF FLYSKLTVDK   360
SRWQQGNVFS CSVMHEALHN HYTQKSLSLS PGK                                393

SEQ ID NO: 25            moltype = DNA    length = 1040
FEATURE                  Location/Qualifiers
source                   1..1040
                         mol_type = other DNA
                         organism = synthetic construct
SEQUENCE: 25
ccttgcttcc tattatatct tcccaaatta ccaatacatt acactagcat ctgaatttca    60
taaccaatct cgatacacca aatcgttcta gaattattac atcaaaacaa aaatggctc   120
gctcgttgg agctaacagt accgttgtgt tggcgatcat cttcttcggt gagtgatttt   180
ccgatcttct tctccgattt agatctcctc tacattgttg cttaatctca gaaccttttt   240
tcgttgttcc tggatctgaa tgtgtttgtt tgcaatttca cgatcttaaa aggttagatc   300
tcgattggta ttgacgattg aatctttacg atttcaggat gttatttgcg ttgtcctct    360
gcaggatcca tgatgactcc tgagaatgat gaagaacaaa catctgtttt ctccgccacg   420
gtttatggag ataaaattca aggaaagaac aaaagaaaac gagtaatagg cggggtggg   480
tcagtcagac taaaccagtg catgtctgca aatgaagcgg caataactga tgctgctgtt   540
gccgtagctg cagcttccag cactcatagg aaagtggcat catctaccac acagtatgat   600
cataaggaga gttgcaatgg ttttgtactat caaggttctt gttatattct tcactcggac   660
taccgctct tttcagacgc aaaagctaat tgtactgcctg agagcagcac actgcccaac   720
aagtctgatg ttcttatcac ttggttaatt gactatgttg aagatacatg gggatcagat   780
ggaaatccaa tcacaaagac taccagtgac taccaagata tgatgtgtc acaagaagtc   840
cgtaagtatt ttgtgtgaa acaatgaat cccggggtg ggaggcag tcaccaccat   900
caccaccatc accaccacca tgatgagctc tagtcgaga atttactca aatgttttg   960
gttgctatgg tagggactat gggttttcg gattccggtg gaagtgagtt gggaggcagt  1020
ggcggaggta agggagttca                                              1040

SEQ ID NO: 26            moltype = DNA    length = 952
FEATURE                  Location/Qualifiers
source                   1..952
                         mol_type = other DNA
                         organism = synthetic construct
SEQUENCE: 26
gccttgcttc ctattatatc tttcccaaatt accaatacat tacactagca tctgaatttc    60
ataaccaatc tcgatacacc aaatcgttct agaattatta catcaaaaca aaaatggct   120
```

```
cgctcgtttg gagctaacag taccgttgtg ttggcgatca tcttcttcgg tgagtgattt    180
tccgatcttc ttctccgatt tagatctcct ctacattgtt gcttaatctc agaaccttt    240
ttcgttgttc ctggatctga atgtgtttgt ttgcaatttc acgatcttaa aaggttagat    300
ctcgattggt attgacgatt ggaatcttta cgatttcagg atgtttattt gcgttgtcct    360
ctgcaggatc ccgcctaaat caatgcatgt ctgctaacga ggctgctatt actgacgccg    420
ctgttgccgt tgctgctgca tcatctactc atagaaaggt tgcgtctagc actacacaat    480
atgatcacaa agaaagctgt aatggtttat attaccaggg ttcttgttat atattacatt    540
cagactacca gttattctcg gatgctaaag caaattgcac tgcggaatca tcaacactac    600
ccaataaatc cgatgtcttg attacctggc tcattgatta tgttgaggat catgggggat    660
ctgatggtaa tccaattaca aaaactacat ccgattatca agattctgat gtatcacaag    720
aagttagaaa gtatttttgt gttaaaacaa tgaaccccg gggtgggga ggcagtcacc    780
accatcacca ccatcaccac caccatgatg agctctagct cgagaatttt actcaaaatgt    840
ttttggttgc tatggtaggg actatggggt tttcggattc cggtggaagt gagttgggag    900
gcagtggcgg aggtaaggga gttcaagatt ctgggaactg aagatttggg gt            952

SEQ ID NO: 27        moltype = DNA  length = 880
FEATURE              Location/Qualifiers
source               1..880
                     mol_type = other DNA
                     organism = synthetic construct
SEQUENCE: 27
gccttgcttc ctattatatc ttcccaaatt accaatacat tacactagca tctgaatttc    60
ataaccaatc tcgatacacc aaatcgttct agaattatta catcaaaaca aaaaatggct   120
cgctcgtttg gagctaacag taccgttgtg ttggcgatca tcttcttcgg tgagtgattt   180
tccgatcttc ttctccgatt tagatctcct ctacattgtt gcttaatctc agaaccttt    240
ttcgttgttc ctggatctga atgtgtttgt ttgcaatttc acgatcttaa aaggttagat   300
ctcgattggt attgacgatt ggaatcttta cgatttcagg atgtttattt gcgttgtcct   360
ctgcaggatc ctctactcat agaaaggttg cgtctagcac tacacaatat gatcacaaag   420
aaagctgtaa tggtttatat taccaggtt cttgttatat tacattcag actaccagt     480
tattctcgga tgctaaagca aattgcactg cggaatcacc aacactaccc aataaatccg   540
atgtcttgat tacctggctc attgattatg ttgaggatac atggggatct gatggtaatc   600
caattacaaa aactacatcc gattatcaag attctgatgt atcacaagaa gttagaaagt   660
attttttgtgt taaaacaatg aaccccgg gtggggagg cagtcaccac catcaccacc    720
atcaccacca ccatgatgag ctctagctcg agaatttttc aaaatgtt ttggttgcta     780
tggtagggac tatgggttt tcggattccg gtggaagtga gttgggaggc agtggcgag   840
gtaagggagt tcaagattct gggaactgaa gatttgggt                           880

SEQ ID NO: 28        moltype = DNA  length = 1040
FEATURE              Location/Qualifiers
source               1..1040
                     mol_type = other DNA
                     organism = synthetic construct
SEQUENCE: 28
gccttgcttc ctattatatc ttcccaaatt accaatacat tacactagca tctgaatttc    60
ataaccaatc tcgatacacc aaatcgttct agaattatta catcaaaaca aaaaatggct   120
tcctctatgc tctcttccgc tactatggtt gcctctccgg ctcaggccac tatggtcgct   180
ccttcaacg gacttaagtc ctccgctgcc ttcccagcca cccgcaaggc taacaacgac   240
actacttcca tcacaagcaa cggcggaaga gttaactgca tgcaggtgtg gcctccgatt   300
ggaaagaaga agtttgagac tctctcttac cttcctgacc ttaccggatc catgatgaca   360
ccagaaaacg acgaagagca gacatctgtg ttctccgcta ctgtttacgg agacaaaatt   420
cagggaagaa ataaacgcaa acgcgtgatt ggaggaggga gttcagtgcg cctaaatcaa   480
tgcatgtctg ctaacgaggc tgctattact gacgccgctg ttgccgttgc tgctgcatca   540
tctactcata gaaaggttgc gtctagcact acacaatatg atcacaaaga aagctgtaat   600
ggtttatatt accaggtttc ttgttatata ttacattcag actaccagtt attctcggat   660
gctaaagcaa attgcactgc ggaatcatca acactaccca ataaatccga tgtcttgatt   720
acctggctca ttgattatgt tgaggataca tggggatctg atggtaatcc aattacaaaa   780
actacatccg attatcaaga ttctgatgta tcacaagaag ttagaaagta ttttttgtgtt   840
aaaacaatga accccgggg tggggaggc agtcaccacc atcaccacca tcaccaccac     900
cattagctcg agaatttttac tcaaaatgtt ttggttgcta tggtagggac tatgggttt   960
tcggattccg gtggaagtga gttgggaggc agtggcggag gtaagggagt tcaagattct   1020
gggaactgaa gatttgggt                                                 1040

SEQ ID NO: 29        moltype = DNA  length = 886
FEATURE              Location/Qualifiers
source               1..886
                     mol_type = other DNA
                     organism = synthetic construct
SEQUENCE: 29
gccttgcttc ctattatatc ttcccaaatt accaatacat tacactagca tctgaatttc    60
ataaccaatc tcgatacacc aaatcgttct agaattatta catcaaaaca aaaaatggga   120
tccatgatga caccagaaaa cgacgaagag cagacatctg tgttctccgc tactgtttac   180
ggagacaaaa ttcagggaaa gaataaacgc aaacgcgtga ttggaggagg gggttcagtg   240
cgcctaaatc aatgcatgtc tgctaacgag gctgctatta ctgacgccgc tgttgccgtt   300
gctgctgcat catctactca tagaaaggtt gcgtctagca ctacacaata tgatcacaaa   360
gaaagctgta atggtttata ttaccaggt tcttgttata ttacattca gactaccag     420
ttattctcgg atgctaaagc aaattgcact gcggaatcat caacactacc aataaatcc   480
gatgtcttga ttacctggct cattgattat gttgaggata catggggatc tgatggtaat   540
ccaattacaa aaactacatc cgattatcaa gattctgatg tatcacaaga agttagaaag   600
tattttttgtg ttaaaacaat gaaccccgg ggtgggagg gcagtcacca ccatcaccac   660
```

```
catcaccacc accattagct cgagaatttt actcaaaatg tttttggttgc tatggtaggg    720
actatggggt tttcggattc cggtggaagt gagttgggag gcagtggcgg aggtaaggga    780
gttcaagatt ctgggaactg aagatttggg gttttgcttt tgaatgtttg tgtttttgta    840
tgatgcctct gtttgtgaac tttgatgtat tttatctttg tgtgaa                   886

SEQ ID NO: 30          moltype = DNA   length = 1680
FEATURE                Location/Qualifiers
source                 1..1680
                       mol_type = other DNA
                       organism = synthetic construct
SEQUENCE: 30
gccttgcttc ctattatatc ttcccaaatt accaatacat tacactagca tctgaatttc     60
ataaccaatc tcgatacacc aaatcgttct agaattatta catcaaaaca aaaaatggct    120
cgctcgtttg gagctaacag taccgttgtg ttggcgatca tcttcttcgg tgagtgattt    180
tccgatcttc ttctccgatt tagatctcct ctacattgtt gcttaatctc agaacctttt    240
ttcgttgttc ctggatctga atgtgtttgt ttgcaattc acgatcttaa aaggttagat    300
ctcgattggt attgacgatt ggaatcttta cgatttcagg atgttatttg cgttgtcctc    360
tgcaggatcc atgatgacac cagaaaacga cgaagagcga acatctgtgt tctccgctac    420
tgtttacgga gacaaaattc agggaaagaa taaacgcaaa cgcgtgattg gaggaggggg    480
ttcagtgcgc ctaaatcaat gcatgtctgc taacgaggct gctattactg acgccgctgt    540
tgccgttgct gctgcatcat ctactcatag aaaggttgcg tctagcacta cacaatatga    600
tcacaaagaa agctgtaatg gtttatatta ccagggtct tgttatatat tacattcaga    660
ctaccagtta ttctcggatg ctaaagcaaa ttgcactgcg gaatcatcaa cactacccaa    720
taaatccgat gtcttgatta cctggctcat tgattatgtt gaggatacat ggggatctga    780
tggtaatcca attacaaaaa ctacatccga ttatcaagat tctgatgtat cacaagaagt    840
tagaaagtat ttttgtgtta aaacaatgaa cccccgggct ccaccttgcc cagctcctga    900
attgcttgga ggtccttctg tttttctttt tccacctaag ccaaaagata cattgatgat    960
ttctaggaca cctgaggtta cttgcgttgt tgttgatgtt tcacatgaag atccagaggt   1020
taagtttaat tggtacgttg atggagttga agttcataat gctaagacta aaccaaggga   1080
agagcaatac gcctctacat acagagttgt ttcagttttg actgttcttc atcaagattg   1140
gcttaacgga aaggaataca agtgtaaagt ttctaacaag gctttgccag ctccatcga   1200
aaagacaatt tcaaaggcta aaggtcaacc aagggagcct caagtttaca ctcttccacc   1260
atcaagagat gaattgacaa agaaccaagt ttcattgact tgccttgtta agggattcta   1320
cccttctgat attgctgttg aatgggagtc aaacggtcaa ccagaaaaca actacaagac   1380
tacaccacct gttcttgatt ctgatggatc tttcttttct tactctaaac ttactgttga   1440
taagtcaaga tggcaacagg gtaatgtttt ctcttgttca gttatgcacg aggcacttca   1500
caatcactac acacaaaaat ctttatcttt atcacctggt aaataactcg agaattttac   1560
tcaaaatgtt ttggttgcta tggtagggac tatgggtttt tcggattccg gtggaagtga   1620
gttgggaggc agtggcggag gtaagggagt tcaagattct gggaactgaa gatttggggt   1680
```

VACCINIA VIRUS RECOMBINANT A33R PROTEIN AND KIT FOR DIAGNOSING ANTIBODIES AGAINST ORTHOPOXVIRUS COMPRISING THE SAME

STATEMENT OF GOVERNMENTAL SUPPORT

The invention was made with government support under Serial No. UI230002TD entitled "Development of plant-based vaccine to counter biological weapons" from the Agency for Defense Development (Republic of Korea).

CROSS-REFERENCE TO RELATED APPLICATION

This application claims priority to and the benefit of Korean Patent Application No. 10-2023-0138774, filed on Oct. 17, 2023, the disclosure of which is incorporated herein by reference in its entirety.

SEQUENCE LISTING

This application contains a Sequence Listing which has been submitted electronically in XML format and is hereby incorporated by reference in its entirety. Said XML copy, created on Apr. 26, 2024, is named SOP116437US_Sequence Listing.xml and is 41,716 bytes in size.

TECHNICAL FIELD

The present invention relates to a vaccinia virus recombinant A33R protein and a kit for diagnosing antibodies against orthopoxvirus comprising the same, and more particularly, to a recombinant A33R protein in which the transmembrane domain of the vaccinia virus A33R protein is replaced with a peptide linker, a recombinant vector for efficiently expressing the recombinant A33R protein, a transgenic organism, a method for producing the recombinant A33R protein, a composition and kit for diagnosing antibodies against orthopoxvirus comprising the recombinant A33R protein.

BACKGROUND ART

Smallpox is an acute disease characterized by fever, blisters, and pustular pathological skin changes, and is caused by the smallpox virus. The mortality rate is very high, and at one time it accounted for 10% of all deaths worldwide, including in Korea. However, in 1979, smallpox was declared an extinct disease worldwide. However, since one case of monkeypox was reported in the UK on May 7, 2022, cases of infection have been reported in many countries, including the US, Brazil, Spain, France, and Colombia, and there has been renewed interest recently as the possibility of the smallpox virus being used as a biological terrorist weapon became known.

In Korea, monkeypox was designated as a level 2 infectious disease on Jun. 8, 2022, and in June of the same year, as a Korean national who visited Germany was finally confirmed to be positive for monkeypox, the crisis situation was raised from 'concern' to 'caution'. As overseas movement becomes more active, the possibility of additional influx cannot be ruled out, and in an unusual international epidemic situation as it is difficult to diagnose based on clinical symptoms alone, the role of rapid and accurate laboratory diagnostic tests for early detection of monkeypox and prevention of community spread is important.

Meanwhile, A17L, A27L, A28L, A33R, B5R, D8L, L1R, and H3 have been reported as vaccinia virus proteins identified as targets of neutralizing antibodies in humans (Non-patent Document 1).

Under this background, the present inventors developed a recombinant vector to produce A33R, one of the major antigens of vaccinia virus, with high efficiency in plants, and demonstrated the serological diagnostic performance of the recombinant A33R protein produced using the recombinant vector, thereby completed the present invention.

[Related Art Document]

Non-Patent Document (Non-patent Document 0001) Ahmed SF, Sohail MS, Quadeer AA, Mckay MR. Vaccinia-Virus-Based Vaccines Are Expected to Elicit Highly Cross-Reactive Immunity to the 2022 Monkeypox Virus. Viruses. 2022 Sep. 3;14 (9): 1960. (3 Sep. 2022)

SUMMARY OF THE INVENTION

Technical Problem

The present invention has been devised to solve the above-mentioned problems, and is directed to providing a gene construct designed to enable the vaccinia virus A33R antigen protein to be expressed in a soluble form while maintaining its inherent immunogenicity.

The present invention is also directed to providing a vaccinia virus A33R antigen protein produced using a recombinant vector and/or a transgenic organism comprising the gene construct, and a composition and kit for diagnosing antibodies against orthopoxvirus comprising the same.

Furthermore, the present invention is directed to a method of diagnosing antibodies against orthopoxvirus by using a vaccinia virus A33R antigen protein produced using the recombinant vector and/or the transgenic organism comprising the gene construct.

However, the technical problems to be achieved in the present invention are not limited to the problems mentioned above, and other problems not mentioned will be clearly understood by those of ordinary skill in the art from the following description.

Technical Solution

In order to solve the above problems, the present invention provides a gene construct, comprising: a polynucleotide encoding a vaccinia virus recombinant A33R protein comprising an amino acid sequence where amino acid residues from positions 34 to 56 in the amino acid sequence of SEQ ID NO: 1 are substituted with a peptide linker.

In the present invention, the peptide linker may be (GGGGS) n (SEQ ID NO: 4), where n is an integer from 1 to 5.

In the present invention, the recombinant A33R protein may comprise the amino acid sequence of SEQ ID NO: 2.

In the present invention, the gene construct may further comprise a polynucleotide encoding an endoplasmic reticulum (ER) signal peptide and/or a polynucleotide encoding an endoplasmic reticulum (ER) retention signal peptide.

In the present invention, the gene construct may further comprise a polynucleotide encoding a His-tag and/or a polynucleotide encoding a peptide linker.

In the present invention, the polynucleotide encoding the endoplasmic reticulum (ER) signal peptide may comprise the nucleotide sequence of SEQ ID NO: 5.

In the present invention, the endoplasmic reticulum retention signal peptide may comprise the amino acid sequence of HDEL (His-Asp-Glu-Leu) (SEQ ID NO: 6), HEEL (His-Glu-Glu-Leu) (SEQ ID NO: 7), KDEL (Lys-Asp-Glu-Leu) (SEQ ID NO: 8), KEEL (Lys-Glu-Glu-Leu) (SEQ ID NO: 9), RDEL (Arg-Asp-Glu-Leu) (SEQ ID NO: 10) or REEL (Arg-Glu-Glu-Leu) (SEQ ID NO: 11).

In the present invention, the peptide linker may be (GGGGS) n (SEQ ID NO: 4), where n is an integer from 1 to 5.

In the present invention, the gene construct may be one in which the following (i) to (v) are linked sequentially:
  (i) the polynucleotide encoding an endoplasmic reticulum signal peptide,
  (ii) the polynucleotide encoding the recombinant A33R protein,
  (iii) the polynucleotide encoding the peptide linker,
  (iv) the polynucleotide encoding a His-tag, and
  (v) the polynucleotide encoding an endoplasmic reticulum (ER) retention signal peptide.

In the present invention, the gene construct may comprise the nucleotide sequence of SEQ ID NO: 13.

The present invention also provides a recombinant vector comprising the gene construct according to the present invention, and a transgenic organism transformed with the recombinant vector.

In the present invention, the transgenic organism may be a plant.

The present invention also provides a method for producing a vaccinia virus recombinant antigen protein, comprising the following (a) and (b):
  (a) transforming the recombinant vector according to the present invention into a plant; and
  (b) isolating and purifying a vaccinia virus recombinant A33R protein from the plant.

In the present invention, the vaccinia virus recombinant A33R protein may be expressed in a soluble form in the plant.

Additionally, the present invention provides a vaccinia virus recombinant antigen protein comprising the amino acid sequence of SEQ ID NO: 2.

In the present invention, the vaccinia virus recombinant antigen protein may be produced using the recombinant vector according to the present invention.

Additionally, the present invention provides a composition and kit for diagnosing antibodies against orthopoxvirus containing the vaccinia virus recombinant A33R protein according to the present invention.

In the present invention, the vaccinia virus recombinant A33R protein may be produced using the recombinant vector according to the present invention.

Furthermore, the present invention provides a method of diagnosing antibodies against orthopoxvirus, comprising the following steps:
  (a) contacting a biological sample isolated from an individual with the above-described vaccinia virus recombinant A33R protein; and
  (b) confirming whether the vaccinia virus recombinant A33R protein binds to specific antibodies against orthopoxvirus in the biological sample through an antigen-antibody reaction.

Advantageous Effects

A vaccinia virus recombinant A33R protein produced using a recombinant vector containing the gene construct according to the present invention is expressed in a soluble form in a plant expression system while maintaining the inherent immunogenicity of the antigen, making it easy to isolate and purify. In addition, using the vaccinia virus recombinant A33R protein according to the present invention, specific antibodies against the vaccinia virus A33R antigen present in serum can be detected through antigen-antibody reaction, and it can be used for diagnosis of antibodies against orthopoxvirus.

BRIEF DESCRIPTION OF THE DRAWINGS

FIG. 1 shows a gene construct encoding a vaccinia virus recombinant A33R protein (A33RdTM), a nucleotide sequence thereof (SEQ ID NO: 25), and an amino acid sequence of the expressed recombinant A33R protein (SEQ ID NO: 14). SEQ ID NO: 13 is an additional nucleotide sequence thereof of the gene construct shown in FIG. 1.

FIG. 4 shows gene constructs encoding various forms of vaccinia virus A33R antigens.

Figure 5:
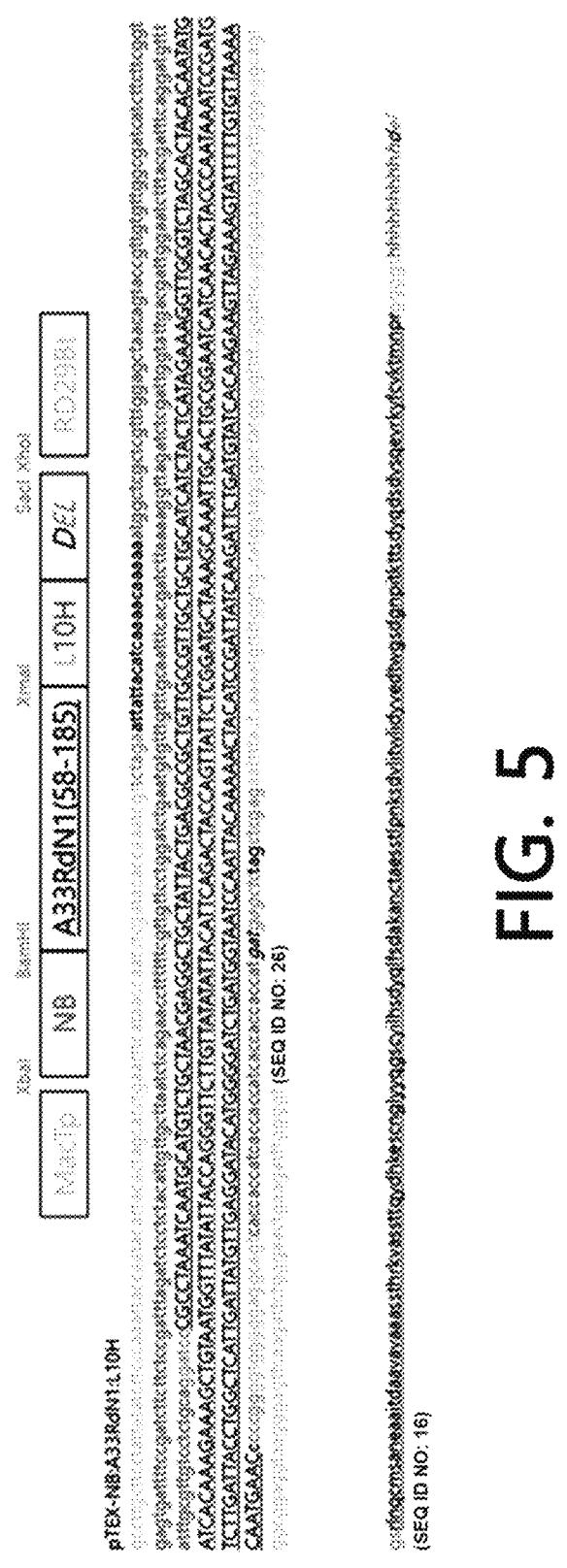

FIG. 5 shows a gene construct encoding the C-terminus of the TMD of the vaccinia virus A33R protein [N-terminus deletion; Positions 58-185 in the amino acid sequence of SEQ ID NO: 1; A33RdN1 (58-185)], a nucleotide sequence thereof (SEQ ID NO: 26), and an amino acid sequence of the expressed recombinant A33RdN1 protein (SEQ ID NO: 16). SEQ ID NO: 15 is an additional nucleotide sequence thereof of the gene construct shown in FIG. 5.

Figure 6:
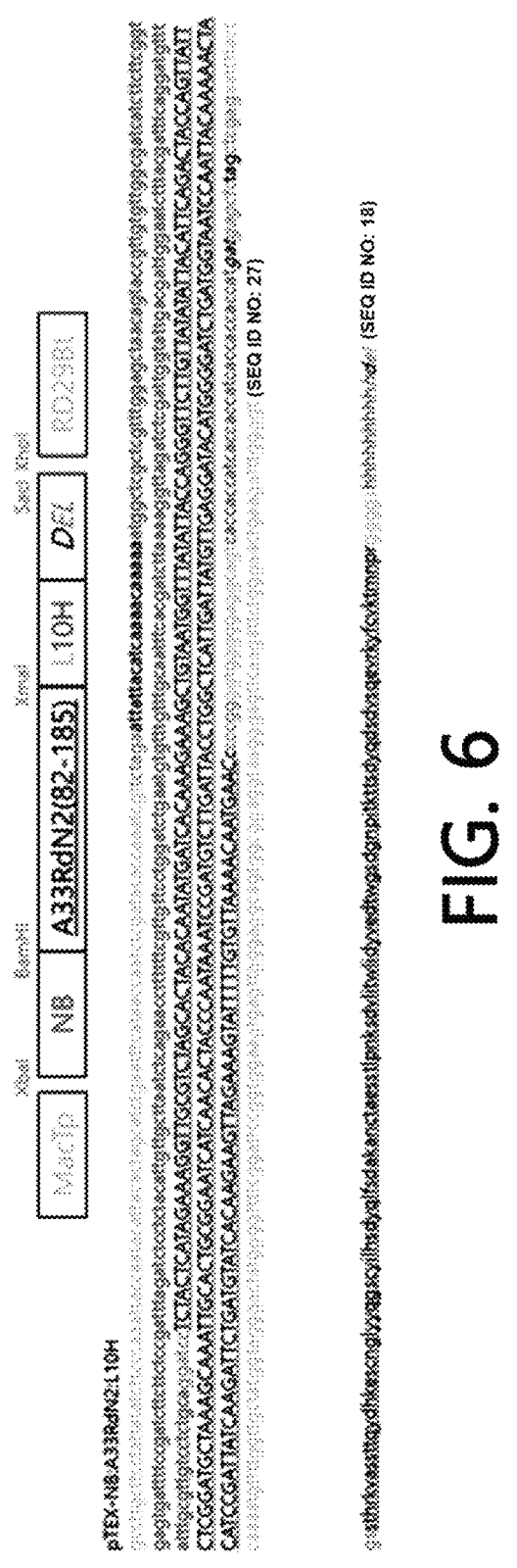

FIG. 6 shows a gene construct encoding the C-terminus of the TMD of the vaccinia virus A33R protein [Additional N-terminus deletion; Positions 82-185 in the amino acid sequence of SEQ ID NO: 1; A33RdN2 (82-185)], a nucleotide sequence thereof (SEQ ID NO: 27), and an amino acid sequence of the expressed recombinant A33RdN2 protein (SEQ ID NO: 18). SEQ ID NO: 17 is an additional nucleotide sequence thereof of the gene construct shown in FIG. 6.

Figure 7:
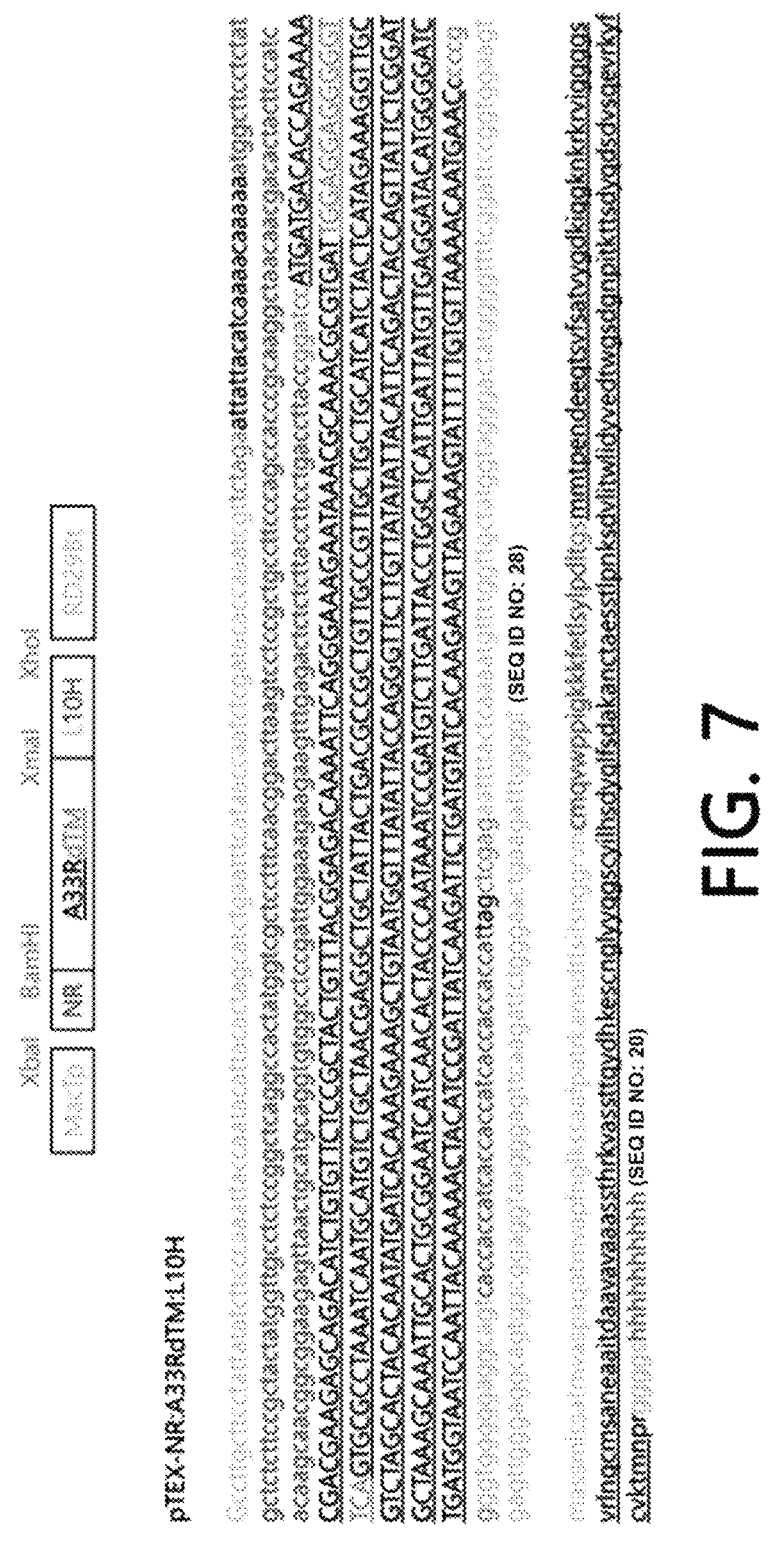

FIG. 7 shows a gene construct for targeting vaccinia virus recombinant A33R protein (A33RdTM) to chloroplasts [pTEX-NR: A33RdTM: L10H], a nucleotide sequence thereof (SEQ ID NO: 28), and an amino acid sequence of the expressed recombinant A33R protein (SEQ ID NO: 20). SEQ ID NO: 19 is an additional nucleotide sequence thereof of the gene construct shown in FIG. 7.

FIG. 8 shows a gene construct for targeting vaccinia virus recombinant A33R protein (A33RdTM) to cytosols [pTEX-A33RdTM: L10H], a nucleotide sequence thereof (SEQ ID NO: 29), and an amino acid sequence of the expressed recombinant A33R protein (SEQ ID NO: 22). SEQ ID NO: 21 is an additional nucleotide sequence thereof of the gene construct shown in FIG. 8.

Figure 9:
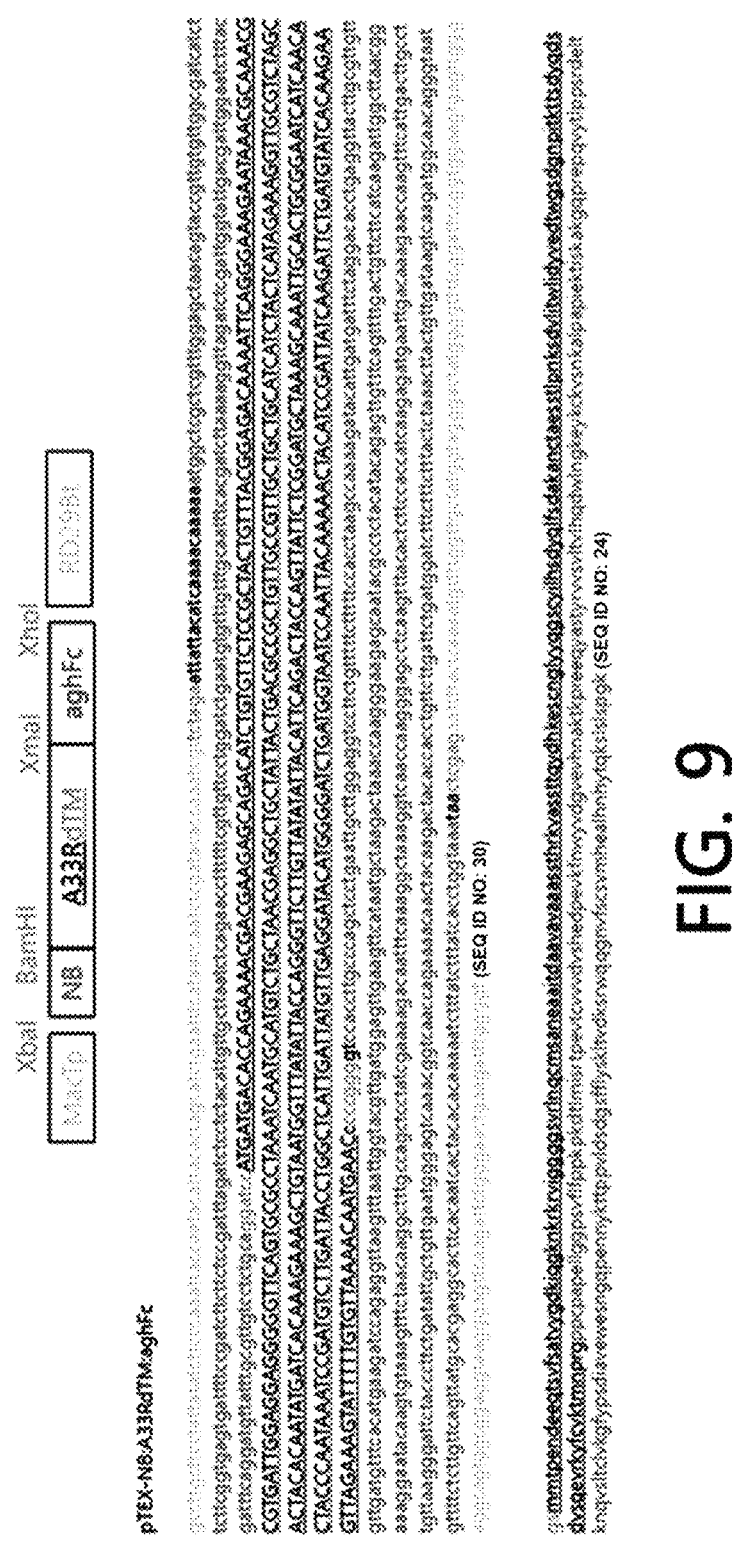

FIG. 9 shows a gene construct encoding a recombinant protein in which human IgG Fc is fused (non-glycosylated) to the C-terminus of the A33R protein [pTEX-NB: A33RdTM: aghFc], a nucleotide sequence thereof (SEQ ID NO: 30), and an amino acid sequence of the expressed recombinant protein (SEQ ID NO: 24). SEQ ID NO: 23 is an additional nucleotide sequence thereof of the gene construct shown in FIG. 9.

DETAILED DESCRIPTION OF THE EMBODIMENTS

Figure 2:
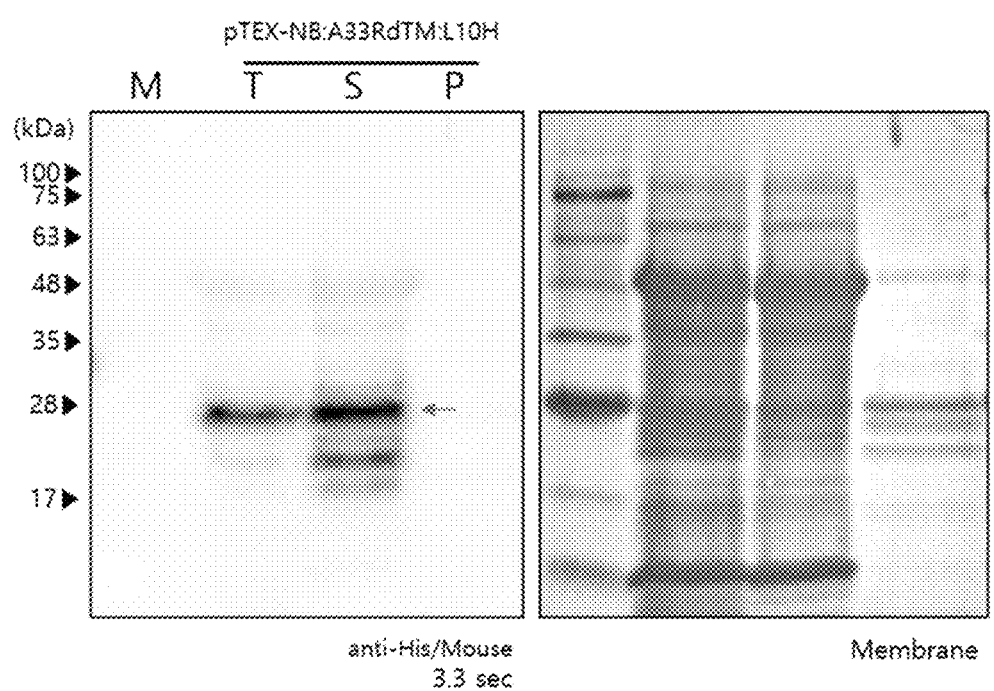
FIG. 2 is a photograph of a band obtained by performing Western blot to confirm the expression of recombinant A33R protein (A33RdTM) (T, Total extract; S, Soluble; P, Pellet).

Unless otherwise defined, all technical and scientific terms used in this specification have the same meaning as commonly understood by a person skilled in the art to which the present invention pertains. In general, the nomenclature used in this specification is well known and commonly used in the art.

As mentioned above, with cases of monkeypox infection occurring simultaneously around the world starting in 2022, the possibility that the smallpox virus will be used as a bioterrorism weapon is emerging, and so the development of a rapid and accurate diagnostic kit is necessary to prepare for this, and there have been no reported cases yet in which a kit was developed to diagnose antibodies specific to orthopoxvirus using the major antigenic protein of vaccinia virus, which was identified as the target of neutralizing antibodies in humans.

Accordingly, in the present invention, in order to produce A33R, one of the main antigens of vaccinia virus, in a water-soluble form in plants with high efficiency, a gene construct encoding a recombinant A33R protein in which the transmembrane domain (TMD) of A33R was replaced with a peptide linker was made, and by confirming that antibodies recognizing the recombinant A33R protein in serum isolated from individuals who received a second-generation smallpox vaccine showed higher antibody binding than other major antigen proteins through indirect enzyme-linked immunosorbent assay (ELISA), the diagnostic performance of the recombinant A33R protein was demonstrated.

Therefore, a first aspect of the present invention relates to a gene construct comprising a polynucleotide encoding a vaccinia virus recombinant A33R protein comprising an amino acid sequence where amino acid residues from positions 34 to 56 in the amino acid sequence of SEQ ID NO: 1 are substituted with a peptide linker.

In the present invention, the amino acid sequence of SEQ ID NO: 1 is an amino acid sequence constituting the vaccinia virus A33R protein, and may be known, for example, as GenBank: AAF63733.1 in an open database such as NCBI.

In the present invention, the region corresponding to amino acid residues from positions 34 to 56 in the amino acid sequence of SEQ ID NO: 1 may be substituted with a peptide linker to express the A33R protein in a water-soluble form.

In this case, the peptide linker is a commonly used GS (Gly-Ser) linker, preferably may be (GGGGS) n (SEQ ID NO: 4), where n may be an integer of 1 to 5, but is not limited thereto.

In the present invention, the recombinant A33R protein may comprise or consist of an amino acid sequence in which amino acid residues from positions 34 to 56 in the amino acid sequence of SEQ ID NO: 1 are substituted with (GGGGS) n (SEQ ID NO: 4) (where n is an integer of 1 to 5). Preferably, it may comprise or consist of the amino acid sequence of SEQ ID NO: 2, wherein the amino acid residues from positions 34 to 56 in the amino acid sequence of SEQ ID NO: 1 are substituted with GGGGS, but substantially, it may be included without limitation as long as it comprises or consists of an amino acid sequence that is the same as that of the recombinant A33R protein or exhibits a corresponding efficacy. Specifically, it may include an amino acid sequence having sequence homology of 70% or more, preferably 80% or more, more preferably 90% or more, and most preferably 95% or more with the amino acid sequence of SEQ ID NO: 2. For example, it includes an amino acid sequence with 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence homology. The "% sequence homology" for an amino acid sequence is determined by comparing a comparison region with two optimally arranged sequences, and parts of the amino acid sequence in the comparison region may include additions or deletions (i.e., gaps) compared to reference sequences (not including additions or deletions) for the optimal arrangement of the two sequences.

In the present invention, the polynucleotide encoding the recombinant A33R protein may comprise or consist of a nucleotide sequence of SEQ ID NO: 3, but substantially, it may be included without limitation as long as it comprises or consists of a nucleotide sequence that is the same as the above nucleotide sequence or exhibits a corresponding efficacy. Specifically, it may include a nucleotide sequence having sequence homology of 70% or more, preferably 80% or more, more preferably 90% or more, and most preferably 95% or more with the nucleotide sequence of SEQ ID NO: 3. For example, it includes a nucleotide sequence with 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence homology. The "% sequence homology" for a nucleotide sequence is determined by comparing a comparison region with two optimally arranged sequences, and parts of the nucleotide sequence in the comparison region may include additions or deletions (i.e., gaps) compared to reference sequences (not including additions or deletions) for the optimal arrangement of the two sequences.

As used herein, the term "polynucleotide" refers to an oligomer or polymer containing two or more linked nucleotides or nucleotide derivatives, including deoxyribonucleic acid (DNA) and ribonucleic acid (RNA), generally linked to each other by phosphodiester bonds. Polynucleotides also include DNA and RNA derivatives including, for example, nucleotide analogues, or "skeleton" bonds other than phosphodiester bonds, such as phosphotriester bonds, phosphoramidate bonds, phosphorothioate bonds, thioester bonds, or peptide bonds (peptide nucleic acids). Polynucleotides include single-stranded and/or double-stranded polynucleotides, such as deoxyribonucleic acid (DNA) and ribonucleic acid (RNA), as well as analogues of either RNA or DNA.

The present invention also includes polynucleotides and fragments thereof having a nucleotide sequence substantially identical to the above nucleotide sequence. A polynucleotide having a substantially identical nucleotide sequence refers to a gene encoding a recombinant protein having the same function as that used in the present invention, regardless of sequence homology. The fragment of the polynucleotide also refers to a polynucleotide encoding a recombinant protein having the same function as that used in the present invention, regardless of the length of the fragment.

In addition, the amino acid sequence of the recombinant protein of the present invention can be obtained from biological resources such as various microorganisms to the extent that it does not affect the immunogenicity (antigenicity) of the protein, and proteins obtained from such other biological resources are also included within the scope of the present invention.

Therefore, the present invention also includes polypeptides and fragments of the polypeptides having substantially the same amino acid sequence as the recombinant A33R protein. A polypeptide having a substantially identical amino acid sequence refers to a protein having the same function as that used in the present invention, regardless of the homology of the amino acid sequence. The fragment of the polypeptide also refers to a protein having the same function as that used in the present invention, regardless of the length of the fragment.

The protein used in the present invention may have some amino acids substituted, and the amino acid substitutions in the present application may be non-conservative substitutions. The non-conservative substitutions may include altering the amino acid residues of the target protein or polypeptide in a non-conservative manner, such as, for example, replacing amino acid residues with a particular side chain size or a particular property (e.g., hydrophilicity) with amino acid residues with different side chain sizes or different properties (e.g., hydrophobicity).

The amino acid substitutions may also be conserved substitutions. The conserved substitutions may include altering the amino acid residues of the target protein or polypeptide in a conserved manner, such as, for example, replacing amino acid residues with a particular side chain size or a particular property (e.g., hydrophilicity) with amino acid residues with the same or similar side chain size or the same or similar property (e.g., still hydrophilicity). These conserved substitutions generally do not significantly affect the structure or function of the produced protein. In the present application, amino acid sequence variants, fragments thereof, or variants thereof substituted with one or more amino acids, which are mutants of recombinant proteins may include conserved amino acid substitutions that do not significantly change the structure or function of the protein.

For example, mutual substitutions between amino acids in each of the following groups may be considered conservative substitutions in this application:

A group of amino acids with non-polar side chains: alanine, valine, leucine, isoleucine, proline, phenylalanine, tryptophan and methionine.

A group of uncharged amino acids with polar side chains: glycine, serine, threonine, cysteine, tyrosine, asparagine and glutamine.

A group of negatively charged amino acids with polar side chains: aspartic acid and glutamic acid.

A group of positively charged basic amino acids: lysine, arginine, and histidine.

A group of amino acids with phenyl: phenylalanine, tryptophan and tyrosine.

The recombinant protein, polypeptide and/or amino acid sequence comprised in the present invention may also be understood to include at least the following ranges: variants or homologues having the same or similar function as the recombinant protein or polypeptide.

In the present invention, compared to the amino acid sequence of the recombinant protein and/or the polypeptide, the variant may be a protein or polypeptide produced by substitution, deletion or addition of one or more amino acids. For example, the functional variant may comprise a protein or polypeptide having an amino acid change by substitution, deletion and/or insertion of at least one amino acid, such as 1-30, 1-20 or 1-10, alternatively, for example, 1, 2, 3, 4, or 5 amino acids. The functional variant may substantially retain the biological properties of the protein or polypeptide prior to the change (e.g., substitution, deletion, or addition). For example, the functional variant may retain at least 60%, 70%, 80%, 90% or 100% of the biological activity of the protein or polypeptide prior to the change.

In the present invention, the homologue may be a protein or polypeptide having at least about 80% (e.g., at least about 85%, about 90%, about 91%, about 92%, about 93%, about 94%, about 95%, about 96%, about 97%, about 98%, about 99% or more) sequence homology to the amino acid sequence of the protein and/or the polypeptide.

In the present invention, the homology generally refers to similarity, analogousness, or association between two or more sequences. The "percent of sequence homology" can be calculated by comparing the two sequences aligned in a comparison window that determines the number of positions where the same nucleotides (e.g., A, T, C, G, I) or the same amino acid residues (e.g., Ala, Pro, Ser, Thr, Gly, Val, Leu, Ile, Phe, Tyr, Trp, Lys, Arg, His, Asp, Glu, Asn, Gln, Cys and Met) exist, and to give the number of matching positions in the comparison window (i.e., window size), the number of matching positions is divided by the total number of positions, and the result is multiplied by 100 to give the percentage of sequence homology. Alignments to determine percent sequence homology can be performed in a variety of ways known in the art, for example, using publicly available computer software such as BLAST, BLAST-2, ALIGN or Megalign (DNASTAR) software. Those skilled in the art can determine appropriate parameters for sequence alignment, including any algorithms necessary to achieve maximal alignment within the full-length sequences being compared or within the target sequence region. The homology can also be determined by the following method: FASTA and BLAST. The FASTA algorithm is disclosed, for example, in W. R. Pearson and D. J. Lipman's "Improved Tool for Biological Sequence Comparison", Proc. Natl. Acad. Sci., 85:2444-2448, 1988; and Lipman, David J., and William R. Pearson. "Rapid and sensitive protein similarity searches." Science 227.4693 (1985): 1435-1441; and the BLAST algorithm is disclosed in S. Altschul, W. Gish, W. Miller, E. W. Myers and D. Lipman, "A Basic Local Alignment Search Tool", Journal of Molecular Biology, 215:403-410, 1990.

The gene construct according to the present invention may further include a polynucleotide encoding an ER (endoplasmic reticulum) signal peptide and/or a polynucleotide encoding an ER retention signal peptide for the purpose of accumulating recombinant A33R protein in an endoplasmic reticulum at a high concentration.

In the present invention, the polynucleotide encoding the endoplasmic reticulum (ER) signal peptide and the polynucleotide encoding the endoplasmic reticulum (ER) retention signal peptide may be located in the 5'-end direction and the 3'-end direction, respectively, of the polynucleotide encoding the recombinant A33R protein.

That is, the endoplasmic reticulum signal peptide and the endoplasmic reticulum retention signal peptide may be linked to the N-terminus and C-terminus, respectively, of the recombinant A33R protein.

In the present invention, the endoplasmic reticulum signal peptide is located at the N-terminus of the recombinant A33R protein and serves to induce the newly synthesized protein to enter the endoplasmic reticulum (ER). The type and amino acid sequence of the endoplasmic reticulum signal peptide according to the present invention are not limited as long as it is a plant endoplasmic reticulum signal peptide known to those skilled in the art, but may be preferably NB (new chaperone binding protein).

In the present invention, the polynucleotide encoding the NB may comprise or consist of a nucleotide sequence of SEQ ID NO: 5, but substantially, it may be included without limitation as long as it comprises or consists of a nucleotide sequence that is the same as the above nucleotide sequence or exhibits a corresponding efficacy. Specifically, it may include a nucleotide sequence having sequence homology of 80% or more, preferably 90% or more, and more preferably 95% or more with the nucleotide sequence of SEQ ID NO: 5.

The NB is used to move the expressed recombinant protein to the endoplasmic reticulum as described above, and when the recombinant A33R protein is expressed, part of the sequence may be cut out and only some amino acids may remain, or the entire sequence may be cut out so that the signal peptide sequence site does not exist.

In the present invention, the endoplasmic reticulum retention signal peptide is located at the C-terminus of the recombinant A33R protein, and when a protein present inside the endoplasmic reticulum escapes to the Golgi apparatus through the secretory pathway, the endoplasmic reticulum retention signal peptide serves to allow the protein to return to the endoplasmic reticulum (retention). The type and amino acid sequence of the endoplasmic reticulum retention signal peptide according to the present invention are not limited as long as it is a plant endoplasmic reticulum retention signal peptide known to those skilled in the art, but it may comprise or consist of preferably HDEL (His-Asp-Glu-Leu) (SEQ ID NO: 6), HEEL (His-Glu-Glu-Leu) (SEQ ID NO: 7), KDEL (Lys-Asp-Glu-Leu) (SEQ ID NO: 8), KEEL (Lys-Glu-Glu-Leu) (SEQ ID NO: 9), RDEL (Arg-Asp-Glu-Leu) (SEQ ID NO: 10) or REEL (Arg-Glu-Glu-Leu) (SEQ ID NO: 11).

In the present invention, the polynucleotide encoding the endoplasmic reticulum retention signal may comprise or consist of a nucleotide sequence encoding HDEL (His-Asp-Glu-Leu) (SEQ ID NO: 6), HEEL (His-Glu-Glu-Leu) (SEQ ID NO: 7), KDEL (Lys-Asp-Glu-Leu) (SEQ ID NO: 8), KEEL (Lys-Glu-Glu-Leu) (SEQ ID NO: 9), RDEL (Arg-Asp-Glu-Leu) (SEQ ID NO: 10) or REEL (Arg-Glu-Glu-Leu) (SEQ ID NO: 11), but substantially, it may be included without limitation as long as it comprises or consists of a nucleotide sequence that is the same as the above nucleotide sequence or exhibits a corresponding efficacy. Specifically, it may include a nucleotide sequence having sequence homology of 80% or more, preferably 90% or more, and more preferably 95% or more with the nucleotide sequence.

Information on the endoplasmic reticulum signal peptide and endoplasmic reticulum retention signal peptide can be referred to literature such as US 20130295065 and WO2009158716.

The gene construct according to the present invention may also further include a polynucleotide encoding a His-tag (SEQ ID NO: 12) for the purpose of purifying the recombinant A33R protein and/or a polynucleotide encoding a peptide linker for the purpose of increasing the binding efficiency between the recombinant A33R protein and Ni-IDA resin.

In the present invention, the polynucleotide encoding a His-tag for purifying the recombinant A33R protein and the polynucleotide encoding a peptide linker for increasing the binding efficiency between the recombinant A33R protein and Ni-IDA resin may be located at the 3' end of the polynucleotide encoding the recombinant A33R protein. Specifically, in the 3' end of the polynucleotide encoding the recombinant A33R protein, it may be located in the order of the polynucleotide encoding a peptide linker for increasing binding efficiency of Ni-IDA resin and the polynucleotide encoding a His-tag for purifying the recombinant A33R protein.

That is, the His-tag for purifying the recombinant A33R protein and the peptide linker for increasing the binding efficiency between the recombinant A33R protein and Ni-IDA resin may be linked to the C-terminus of the recombinant A33R protein. Specifically, in the C-terminus of the recombinant A33R protein, it may be linked in the order of the peptide linker for increasing the binding efficiency of Ni-IDA resin and the His-tag for purifying the recombinant A33R protein.

In the present invention, the His-tag refers to a polyhistidine tag and includes at least 6 histidine residues, preferably may consist of 6 to 20 histidine residues (SEQ ID NO: 12).

In the present invention, the peptide linker for increasing the binding efficiency between the recombinant A33R protein and Ni-IDA resin is a commonly used GS (Gly-Ser) linker, preferably may be (GGGGS) n (SEQ ID NO: 4), where n may be an integer of 1 to 5, but is not limited thereto.

In the present invention, the gene construct may be in the form of the following (i) to (v) linked sequentially:

(i) the polynucleotide encoding an endoplasmic reticulum signal peptide, (ii) the polynucleotide encoding the recombinant A33R protein, (iii) the polynucleotide encoding the peptide linker, (iv) the polynucleotide encoding a His-tag, and (v) the polynucleotide encoding an endoplasmic reticulum (ER) retention signal peptide.

The gene construct of the present invention may further include a promoter, which is a transcription initiation factor that binds to RNA polymerase, a random operator sequence for regulating transcription, a sequence encoding an appropriate mRNA ribosome binding site, a sequence regulating the termination of transcription and decoding, a terminator, a cloning site, etc.

The promoter may include, for example, pEMU promoter, MAS promoter, histone promoter, Clp promoter, 35S promoter derived from cauliflower mosaic virus, 19S RNA promoter derived from cauliflower mosaic virus, plant actin protein promoter, ubiquitin protein promoter, CMV (Cytomegalovirus) promoter, SV4 (Simian virus 40) promoter, RS (Respiratory syncytial virus) promoter, EF-1α (Elongation factor-1 alpha) promoter, pEMU promoter, MAS promoter, histone promoter, Clp promoter, MacT (CaMV 35S+MAS; 3' end nucleotide of Mac promoter is replaced with T) promoter, etc., and the terminator may include, for example, nopaline synthase (NOS), rice amylase RAmyl A terminator, phaseolin terminator, terminator of the octopine gene of *Agrobacterium tumefaciens*, rrnB1/B2 terminator of *E. coli*, HSP18.2 terminator of *Arabidopsis thaliana*, RD29B terminator of *Arabidopsis thaliana*, etc., but those listed above are examples only and are not limited thereto.

The term "cloning site" refers to a generic term that is inserted for the purpose of linking/distinguishing each gene within the vector. Preferably, the cloning site may be a sequence represented by "tctaga", a sequence represented by "ggatcc", a sequence represented by "cccggg", a sequence represented by "gagctc", or a sequence represented by "ctcgag" in the nucleotide sequence of SEQ ID NO: 13, but is not limited thereto.

Figure 1:
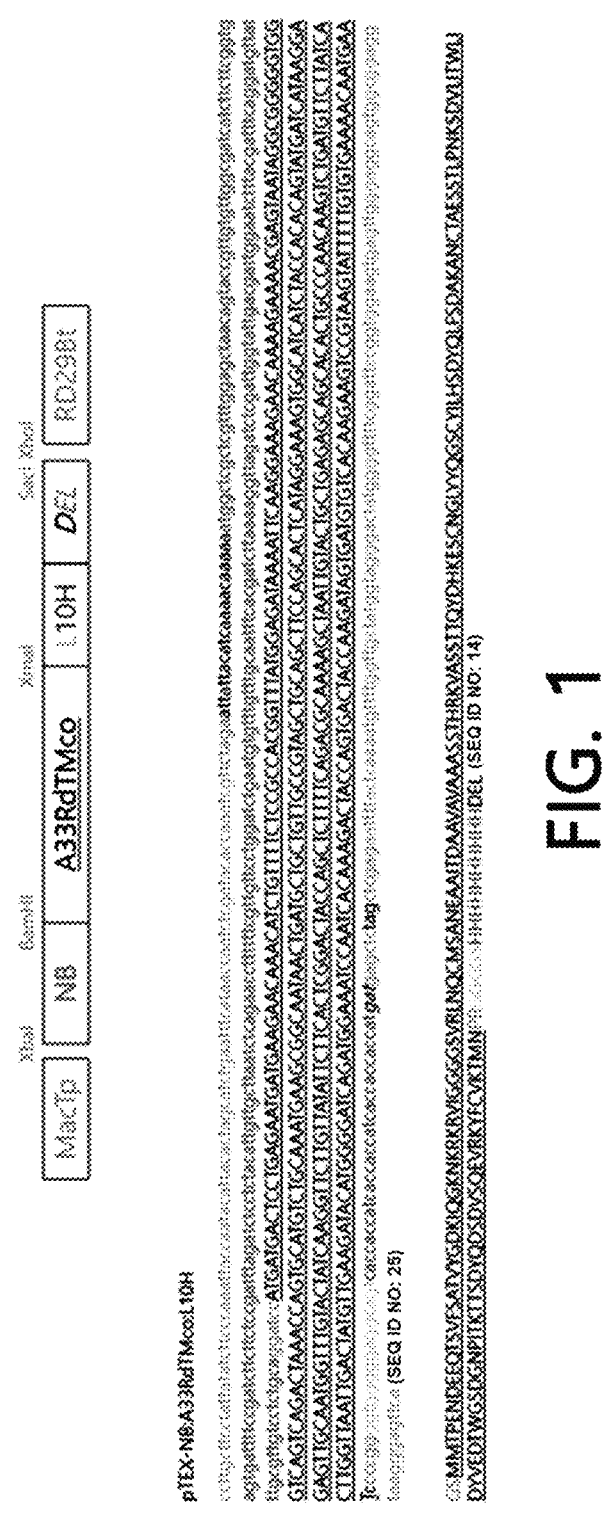

The gene construct according to an embodiment of the present invention may include the expression cassette of FIG. 1. The "expression cassette" refers to a nucleic acid construct containing the elements necessary to express a target product. Specifically, it refers to a nucleic acid construct containing at least an expression regulatory region including a promoter and a nucleic acid for expressing a target product operably linked to the expression regulatory region.

The gene construct containing the expression cassette of FIG. 1 may comprise or consist of the nucleotide sequence of SEQ ID NO: 13.

A second aspect of the present invention relates to a recombinant vector containing the various types of gene constructs according to the present invention, and a transgenic organism transformed therewith.

In the present specification, "recombinant vector" refers to a vector capable of expressing a peptide or protein encoded by a heterogeneous nucleic acid inserted into the vector, and preferably, refers to a vector manufactured to express a target antigen (in the present invention, vaccinia virus recombinant A33R protein). The "vector" refers to any vehicle for the introduction and/or transfer of a base into a host cell in vitro, ex vivo or in vivo, and may be a replicon that can bind to other DNA fragments and result in replication of the combined fragment, in which "replicon" to any genetic unit (e.g., plasmid, phage, cosmid, chromosome, virus, etc.) that functions as a self-unit of DNA replication in vivo, that is, is capable of replication by its own regulation.

The vector used for expression of the gene construct according to the present invention may be any expression vector known in the art.

The recombinant vector according to a specific embodiment of the present invention may be expressed in plants or plant cells, and accordingly, the vector may be a binary vector commonly used for transformation of plants or plant cells.

In the present invention, "plant" can be used without limitation as long as it is a plant capable of mass-producing vaccinia virus recombinant A33R protein, and specifically, it may be one selected from the group consisting of tobacco, *Arabidopsis thaliana*, corn, rice, soybean, canola, alfalfa, sunflower, alfalfa, sorghum, wheat, cotton, peanut, tomato, potato, lettuce and chili pepper, and preferably may be tobacco. The tobacco in the present invention is not particularly limited in type as long as it is a plant of the *Nicotiana* genus and can overexpress proteins, and the present invention can be implemented by selecting an appropriate cultivar according to the transformation method and the purpose of mass production of protein. For example, cultivars such as *Nicotiana benthamiana* L. or *Nicotiana tabacum* cv. Xanthi can be used.

When the recombinant vector according to a specific embodiment of the present invention is expressed in a plant, the gene construct may comprise a nucleotide sequence codon-optimized for the plant, or may comprise a gene construct consisting of the same. For example, when the plant is *Nicotiana benthamiana* L. or *Nicotiana tabacum* cv. Xanthi, the gene construct may comprise or consist of the nucleotide sequence of SEQ ID NO: 13, which is codon-optimized for *Nicotiana benthamiana* L. or *Nicotiana tabacum* cv. Xanthi.

As is well known in the art, in order to increase the expression level of a transgene in a host cell, the gene must be operably linked to transcription and decoding expression regulatory sequences. Preferably, the expression regulatory sequence and the corresponding gene are included in one recombinant vector that also contains a bacterial selection marker and a replication origin. The recombinant vector preferably further contains an expression marker useful in plant cells. Plants or plant cells transformed by the above-described recombinant vector constitute another aspect of the present invention. As used in the present specification, the term "transformation" refers to introducing DNA into a host so that the DNA can be replicable as an extrachromosomal factor or through completion of chromosomal integration. Meanwhile, "transfection" refers to introducing DNA into a host cell so that it can be replicable within the host cell.

Of course, it should be understood that not all vectors are equally functional in expressing gene constructs within the system of the present invention. However, those skilled in the art can make an appropriate selection among various vectors and expression regulatory sequences without excessive experimental burden and without departing from the scope of the present invention. The copy number of the vector, the ability to control copy number and the expression of other proteins encoded by the vector, such as antibiotic markers, should also be considered.

A preferred example of the recombinant vector of the present invention is the Ti-plasmid vector, which can transfer a part of itself, the so-called T-region, into plant cells when present in a suitable host such as *Agrobacterium tumefaciens*. Another type of Ti-plasmid vector (see EP 0 116 718 B1) is currently used to transfer hybrid DNA sequences into plant cells or protoplasts from which new plants can be produced with the hybrid DNA properly inserted into the plant's genome. A particularly preferred form of Ti-plasmid vectors are the so-called binary vectors as claimed in EP 0 120 516 B1 and U.S. Pat. No. 4,940,838. Other suitable vectors that can be used to introduce the gene construct according to the present invention into a plant host may be selected from viral vectors such as those that may be derived from double-stranded plant viruses (e.g., CaMV) and single-stranded viruses, geminiviruses, etc., e.g., non-complete plant virus vectors. The use of such vectors can be particularly advantageous when it is difficult to properly transform plant hosts.

The expression vector will preferably include one or more selectable markers. The marker is a nucleic acid sequence that has characteristics that can be generally selected by chemical methods, and includes all genes that can distinguish transformed cells from non-transformed cells. Examples include, but are not limited to, resistance genes to herbicides such as glyphosate or phosphinothricin, antibiotic resistance genes to antibiotics such as Kanamycin, G418, Bleomycin, hygromycin, chloramphenicol.

In the plant expression vector of the present invention, the promoter can be appropriately selected and used from among the types of promoters described above.

In the present invention, a constitutive promoter may be preferred because selection of transgenic organisms can be accomplished at various stages and by various tissues. The "constitutive promoter" is a promoter that is active under most environmental conditions and developmental states or cell differentiation. Therefore, constitutive promoters do not limit selection possibilities.

In the recombinant vector of the present invention, the terminator can be appropriately selected and used from among the types of terminators described above.

In the present invention, a "transgenic organism" refers to an organism produced by injecting an external gene using molecular genetic methods, and preferably is a living organism transformed by the recombinant expression vector of the present invention, wherein the living organisms are not limited as long as they are living organisms such as microorganisms, eukaryotic cells, insects, animals and plants, and preferably are *Escherichia coli, Salmonella, Bacillus*, yeast, animal cells, mice, rats, dogs, monkeys, pigs, horses, cows, Acrobacterium *tumefaciens*, plants, etc., but are not limited thereto.

In this case, since the type of "plant" is the same as described above, its description is omitted.

The transgenic organism can be produced by methods such as transformation, transfection, *Agrobacterium*-mediated transformation, particle gun bombardment, sonication, electroporation and PEG (Polyethylene glycol)-mediated transformation method, etc., but there is no limitation as long as the method can inject the vector of the present invention.

A third aspect of the present invention relates to vaccinia virus recombinant antigen protein and a method for producing the same.

In the present invention, the vaccinia virus recombinant antigen protein may include the amino acid sequence of SEQ ID NO: 2, or may be a vaccinia virus recombinant A33R protein consisting of the same. The vaccinia virus recombinant A33R protein may be produced using the gene construct according to the first aspect of the present invention, or the recombinant vector or transgenic organism according to the second aspect of the present invention.

Specifically, the method for producing the vaccinia virus recombinant antigen protein of the present invention may include the following steps (a) and (b):

(a) transforming a plant cell or plant with the recombinant vector according to the second aspect of the present invention; and (b) isolating and purifying the vaccinia virus recombinant A33R protein from the plant cell or plant.

In the present invention, the step (a) may include transient expression or stable transformation of the gene construct according to the first aspect in a plant cell or plant transformed through a vector.

In addition to transient expression of the gene construct according to the first aspect in a transformed plant or plant cell, the gene construct may be stably transformed by being introduced into the genome of the transformed plant or plant cell and existing as a chromosomal factor. For those skilled in the art to which the present invention pertains, it will be obvious that inserting the gene targeting the vaccinia virus recombinant A33R protein into the plant genome chromosome will have the same effect.

In the present invention, introduction of the vector comprising the gene construct or chromosomal insertion of the gene construct encoding the vaccinia virus recombinant A33R protein may be performed by adding *Agrobacterium* containing a vector comprising a gene construct encoding the vaccinia virus recombinant A33R protein to a population of plant cells and co-culturing them.

In an embodiment, the co-culture may be performed under dark conditions. The co-culture refers to culturing a culture of plant cells and *Agrobacterium* containing a vector comprising a gene construct encoding the vaccinia virus recombinant A33R protein while stirring, and may further include a stationary culture step.

As such, the gene construct encoding the vaccinia virus recombinant A33R protein can be transiently expressed or stable transformed in plant cells through a vector.

The stationary culture is a method of culturing in a state in which the container is left stationary without stirring the culture medium, and herein, it can be used interchangeably with immersion without stirring.

The stationary culture may be included in the form of a single or intermittent culture.

When a single stationary culture is included, for example, the culture of plant cells and *Agrobacterium* may be co-cultured with stirring, and after stationary culture, the culture may be cultured again with stirring. When intermittent stationary culture is included, a culture form in which plant cells and *Agrobacterium* cultures are co-cultured with stirring, incubated stationary, and then co-cultured with stirring again may be repeated several to dozens of times.

In this case, in detail, the culturing may be characterized by co-culturing the plant cells and a culture of *Agrobacterium* containing the vector comprising a gene construct encoding the vaccinia virus recombinant A33R protein with stirring for 1 minute to 48 hours, then stationary-culturing for 1 minute to 96 hours, and then culturing with stirring for 1 to 10 days again. The OD600 of *Agrobacterium* added for co-culture may be 0.00001 to 2.0.

If the OD600 of *Agrobacterium* is too low, there is a problem that the transformation infection rate for transient expression is low, and if it is too high, there is a problem that the survival rate of host cells drastically decreases. Therefore, it is preferable to co-culture by adding *Agrobacterium* having an OD600 in the above-defined range.

In this case, *Agrobacterium*, which is commonly used for plant transformation, can be used, and for example, *Agrobacterium tumefaciens* or *Agrobacterium rhizogenes* can be used.

Transformation plant refers to any method of transferring DNA to a plant. Such transformation methods do not necessarily require a regeneration and/or tissue culture period. Transformation of plant species is now common for plant species including both monocots as well as dicots. In principle, any transformation method can be used to introduce the hybrid DNA according to the present invention into suitable progenitor cells. The method may be appropriately selected from the calcium/polyethylene glycol method for protoplasts, electroporation of protoplasts, microinjection into plant elements, particle bombardment of various plant elements (DNA or RNA-coated), infection by (non-complete) viruses in *Agrobacterium tumefaciens* mediated gene transfer by invasion of plants or transformation of mature pollen or microspores, and the like. A preferred method according to the present invention involves *Agrobacterium*-mediated DNA transfer.

In the present invention, the vaccinia virus recombinant A33R protein expressed in plant cells or plants may be in a water-soluble form. More specifically, 60%, 65%, 70%, 75%, 80%, 85%, 90%, 91%, 92%, 93%, 94%, 95%, 96%, 97%, 98%, 99% or 100% of the vaccinia virus recombinant A33R protein expressed in the plant cells or plants may be dissolved in the water-soluble fraction.

The step (b) may be to recover the vaccinia virus recombinant A33R protein by purifying the total soluble protein extract obtained by crushing the tissues isolated from the plant cells or plants by affinity chromatography.

A fourth aspect of the present invention relates to a composition and kit for diagnosing orthopoxvirus antibodies comprising the vaccinia virus recombinant A33R protein according to the present invention.

In the present invention, the vaccinia virus recombinant A33R protein can be produced using the recombinant vector according to the second aspect described above.

Figure 11:
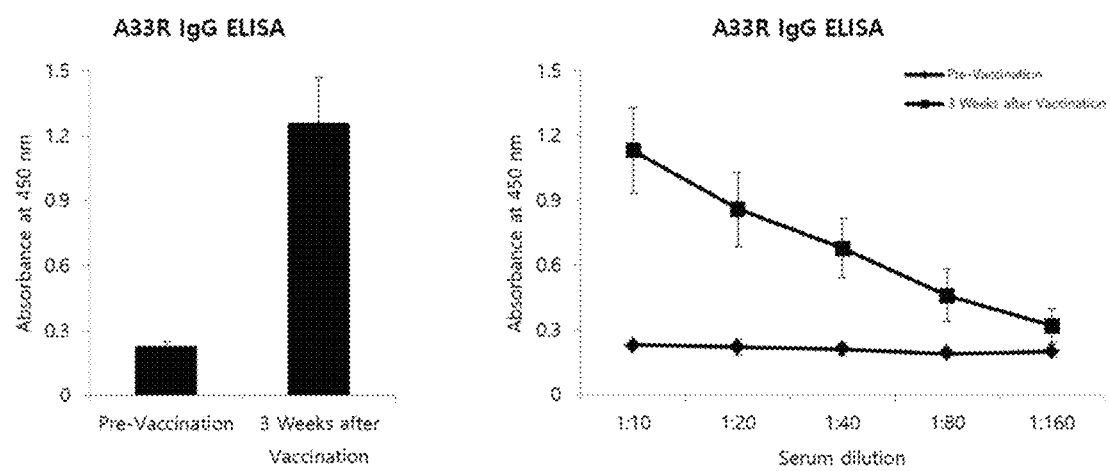
FIG. 11 shows the concentration of vaccinia virus antibodies that recognize the recombinant A33R protein (A33RdTM) in serum isolated from individuals who received a second-generation smallpox vaccine through indirect enzyme-linked immunosorbent assay (ELISA).

In a specific embodiment of the present invention, using the vaccinia virus recombinant A33R protein, it was confirmed that vaccinia virus-specific IgG antibody (A33R IgG antibody) could be effectively detected in serum isolated from a second-generation smallpox vaccine recipient, through antigen-antibody reaction (FIG. 11). As such, the vaccinia virus recombinant A33R protein according to the present invention can diagnose antibodies against orthopoxvirus by detecting antibodies specific to orthopoxvirus present in serum through antiserological test, and can be used as a composition and kit for diagnosing antibodies against orthopoxvirus.

In the present invention, the term "diagnosis" refers to confirming the presence or absence of antibodies formation against orthopoxvirus by detecting IgG antibodies in biological samples isolated from an individual. IgG is produced in large quantities during the secondary immune response and is known to help the phagocytosis of macrophages and neutrophils, so when the test result of the antibody diagnostic kit is positive, it means that IgG antibody was produced and there was a history of orthopoxvirus infection.

In the present invention, the term "kit" refers to a screening device that contains the vaccinia virus antigen as an active ingredient and so provides information on the formation of orthopoxvirus antibodies and the history of orthopoxvirus infection, and it is not limited as long as it is in a form that can confirm the presence of IgG antibodies from a biological sample. Preferably it may comprise the vaccinia virus recombinant A33R protein according to the present invention.

In the present invention, the orthopoxvirus may be smallpox virus, vaccinia virus, cowpox virus, or monkeypox virus.

In the present invention, the composition and kit may further include a chromogenic enzyme, a radioisotope, a chromophore, a luminescent substance, or a fluorescent substance. Specifically, the vaccinia virus recombinant A33R protein may be labeled with a chromogenic enzyme, a radioisotope, a chromophore, a luminescent substance, or a fluorescent substance.

For example, the chromogenic enzyme includes, but is not limited to, peroxidase, alkaline phosphatase, luciferase, etc. The radioisotope includes, but is not limited to, $^{124}$I, $^{125}$I, $^{111}$In, $^{99m}$Tc, $^{32}$P or $^{35}$S. The luminescent substance or fluorescent substance includes, but is not limited to, FITC, RITC, rhodamine, Texas Red, fluorescein, phycoerythrin, or quantum dots.

Recombinant antigen proteins containing the above detectable labels can be detected using conventionally known detection methods for each label. For example, when using a fluorescent signal FITC as a label, a method of measuring fluorescence intensity for each recombinant antigen protein concentration at the maximum wavelength (Excitation: 495 nm, Emission: 520 nm) of FITC linked to recombinant antigen protein may be used, using a fluorometer.

Alternatively, when the vaccinia virus recombinant A33R protein according to the present invention is provided unlabeled, it may contain additional components to confirm whether antibodies against orthopoxvirus is detected. The component may be a known compound for labeling a recombinant antigen protein; or an antibody against the vaccinia virus recombinant A33R protein of the present invention or a specific receptor binding to the protein or a secondary antibody against them, and a reagent for detection thereof, for exploration through an antigen-antibody reaction. Specifically, the diagnosis of the present invention may be performed by modifying a conventional immunoassay method or protocol. For example, the diagnosis of the present invention may be performed by using the recombinant antigen protein of the present invention instead of the antibody in the conventional immunoassay and using the same process. In addition, ELISA (enzyme-linked immunosorbant assay) may be performed with a slight modification to ELONA (enzyme-linked oligonucleotide assay).

In the present invention, the vaccinia virus recombinant A33R protein may be provided in a form coated on the surface of a plate. In this case, after inoculated the target sample directly onto the plate and reacted under appropriate conditions, by confirming the binding to the specific antibodies against orthopoxvirus contained in the target sample on the surface of the plate, it is possible to diagnose whether antibodies against orthopoxvirus are formed and the history of infection.

The composition and kit of the present invention may additionally contain a buffer solution or reaction solution that stably maintains the structure or physiological activity of the recombinant antigen protein. In addition, for maintaining stability, they may be provided in powder form or in a state dissolved in a suitable buffer solution or maintained at a constant temperature such as 4° C.

The kit of the present invention may take the form of a bottle, tub, sachet, envelope, tube, ampoule, etc., and they may be formed partially or entirely from plastic, glass, paper, foil, wax, etc. The container may be equipped with a completely or partially detachable closure that is part of it or that may be attached to the container by mechanical, adhesive or other means. The container may also be equipped with a stopper that allows access to the contents by means of an injection needle.

From another perspective, the fourth aspect of the present invention relates to a method for providing information for diagnosing antibodies against orthopoxvirus, comprising the following steps:
  (a) contacting a biological sample isolated from an individual with the vaccinia virus recombinant A33R protein according to the present invention;
  (b) confirming whether the vaccinia virus recombinant A33R protein binds to specific antibodies against orthopoxvirus in the biological sample through an antigen-antibody reaction.

In the present invention, the term "biological sample" refers to a sample of a subject in which orthopoxvirus or specific antibodies produced by it is likely to be present, and the presence or absence of it needs to be confirmed. Specifically, it may be one isolated from one or more species selected from the group consisting of blood, plasma, serum, lymph, urine, tears, synovial fluid, saliva, wound fluid, and cerebrospinal fluid, for example, may be one isolated from serum, but is not limited thereto.

In the present invention, the method for providing information may further include a color development step of contacting the sample that has undergone the contact step of (a) with a chromogenic enzyme. In this case, the chromogenic enzyme may bind to an antibody against a specific antigen in contact with the sample to produce a color reaction. If this color development does not appear, it means that there are no antibodies against the specific antigen that reacts with the chromogenic enzyme in the sample. In other words, if no color reaction occurs during the color development step, it means that there is no antibody in the sample.

Hereinafter, the present invention will be described in more detail through examples. However, since the present invention may have various changes and may have various forms, the specific examples and descriptions described below are only for helping the understanding of the present invention, and it is not intended to limit the invention to any particular form disclosed. It should be understood that the scope of the present invention includes all modifications, equivalents and substitutes included in the spirit and scope of the present invention.

The amino acid sequences and nucleotide sequences used in the present invention are shown in Table 1 below.

TABLE 1

| Protein/Gene | Sequence | SEQ ID NO |
|---|---|---|
| Vaccinia virus A33R | MMTPENDEEQTSVFSATVYGDKIQGKNKRKRVI GLCIRISMVISLLSMITMSAFLIVRLNQCMSANE AAITDAAVAVAAASSTHRK VASSTTQYDHKESC NGLYYQGSCYILHSDYQLFSDAKANCTAESSTL PNKSDVLITWLIDYVEDTWGSDGNPITKTTSDY QDSDVSQEVRKYFCVKTMN | 1 |
| A33RdTM | MMTPENDEEQTSVFSATVYGDKIQGKNKRKRVI GGGGSVRLNQCMSANEAAITDAAVAVAAASST HRKVASSTTQYDHKESCNGLYYQGSCYILHSDY QLFSDAKANCTAESSTLPNKSDVLITWLIDYVE DTWGSDGNPITKTTSDYQDSDVSQEVRKYFCV KTMN | 2 |
| | ATGATGACTCCTGAGAATGATGAAGAACAAAC ATCTGTTTTCTCCGCCACGGTTTATGGAGATAA AATTCAAGGAAAGAACAAAAGAAAACGAGTA ATAGGCGGGGGTGGGTCAGTCAGACTAAACC AGTGCATGTCTGCAAATGAAGCGGCAATAACT GATGCTGCTGTTGCCGTAGCTGCAGCTTCCAG CACTCATAGGAAAGTGGCATCATCTACCACAC AGTATGATCATAAGGAGAGTTGCAATGGTTTG TACTATCAAGGTTCTTGTTATATTCTTCACTCG GACTACCAGCTCTTTTCAGACGCAAAAGCTAA TTGTACTGCTGAGAGCAGCACACTGCCCAAC AAGTCTGATGTTCTTATCACTTGGTTAATTGAC TATGTTGAAGATACATGGGGATCAGATGGAAA TCCAATCACAAAGACTACCAGTGACTACCAAG ATAGTGATGTGTCACAAGAAGTCCGTAAGTAT TTTTGTGTGAAAACAATGAAT | 3 |
| Peptide linker | (GGGGS)n (where n is an integer from 1 to 5) | 4 |
| NB (new chaperone binding protein) | ATGGCTCGCTCGTTTGGAGCTAACAGTACCGT TGTGTTGGCGATCATCTTCTTCGGTGAGTGATT TTCCGATCTTCTTCTCCGATTTAGATCTCCTCTA CATTGTTGCTTAATCTCAGAACCTTTTTTCGTT GTTCCTGGATCTGAATGTGTTTGTTTGCAATTT CACGATCTTAAAAGGTTAGATCTCGATTGGTAT TGACGATTGGAATCTTTACGATTTCAGGATGTT ATTTGCGTTGTCCTCTGCA | 5 |
| Endoplasmic reticulum retention signal peptide | HDEL | 6 |
| | HEEL | 7 |
| | KDEL | 8 |
| | KEEL | 9 |
| | RDEL | 10 |
| | REEL | 11 |
| His-tag | HHHHHHHHHH | 12 |
| pTEX-NB:A33RdTMco:L10H | tctagaattattacatcaaaacaaaaaatggctcgctcgtttggagctaacag taccgttgtgttggcgatcatcttcttcggtgagtgatttccgatcttcttctcc gatttagatctcctctacattgttgcttaatctcagaaccttttttcgttgttcctg gatctgaatgtgtttgtttgcaatttcacgatcttaaaaggttagatctcgattg gtattgacgattggaatctttacgatttcaggatgttatttgcgttgtcctctgca ggatccATGATGACTCCTGAGAATGATGAAGAAC AAACATCTGTTTTCTCCGCCACGGTTTATGGA GATAAAATTCAAGGAAAGAACAAAAGAAAAC GAGTAATAGGCGGGGGTGGGTCAGTCAGACT AAACCAGTGCATGTCTGCAAATGAAGCGGCA ATAACTGATGCTGCTGTTGCCGTAGCTGCAGC TTCCAGCACTCATAGGAAAGTGGCATCATCTA CCACACAGTATGATCATAAGGAGAGTTGCAAT GGTTTGTACTATCAAGGTTCTTGTTATATTCTTC ACTCGGACTACCAGCTCTTTTCAGACGCAAAA GCTAATTGTACTGCTGAGAGCAGCACACTGCC | 13 |

TABLE 1-continued

| Protein/Gene | Sequence | SEQ ID NO |
|---|---|---|
| | CAACAAGTCTGATGTTCTTATCACTTGGTTAAT TGACTATGTTGAAGATACATGGGGATCAGATG GAAATCCAATCACAAAGACTACCAGTGACTAC CAAGATAGTGATGTGTCACAAGAAGTCCGTAA GTATTTTTGTGTGAAAACAATGAATccccggggtgg gggaggcagtcaccaccatcaccaccatcaccaccaccat*gatgagctct agctcgag* GSMMTPENDEEQTSVFSATVYGDKIQGKNKRK RVIGGGGSVRLNQCMSANEAAITDAAVAVAAAS STHRKVASSTTQYDHKESCNGLYYQGSCYILHS DYQLFSDAKANCTAESSTLPNKSDVLITWLIDY VEDTWGSDGNPITKTTSDYQDSDVSQEVRKYF CVKTMNPRGGGGSHHHHHHHHHHDEL | 14 |
| pTEX-NB:A33RdN1:L10H | tctagaattattacatcaaaacaaaaaatggctcgctcgtttggagctaacag taccgttgtgttggcgatcatcttcttcggtgagtgattttccgatcttcttctcc gatttagatctcctctacattgttgcttaatctcagaaccttttttcgttgttcctg gatctgaatgtgtttgtttgcaatttcacgatcttaaaaggttagatctcgattg gtattgacgattggaatctttacgatttcaggatgtttatttgcgttgtcctctgc aggatccCGCCTAAATCAATGCATGTCTGCTAACG AGGCTGCTATTACTGACGCCGCTGTTGCCGTT GCTGCTGCATCATCTACTCATAGAAAGGTTGC GTCTAGCACTACACAATATGATCACAAAGAAA GCTGTAATGGTTTATATTACCAGGGTTCTTGTT ATATATTACATTCAGACTACCAGTTATTCTCGG ATGCTAAAGCAAATTGCACTGCGGAATCATCA ACACTACCCAATAAATCCGATGTCTTGATTACC TGGCTCATTGATTATGTTGAGGATACATGGGA TCTGATGGTAATCCAATTACAAAAACTACATCC GATTATCAAGATTCTGATGTATCACAAGAAGTT AGAAAGTATTTTTGTGTTAAAACAATGAACccc cggggtggggaggcagtcaccaccatcaccaccatcaccaccaccat*g atgagctc*tagctcgag GSRLNQCMSANEAAITDAAVAVAAASSTHRKVA SSTTQYDHKESCNGLYYQGSCYILHSDYQLFSD AKANCTAESSTLPNKSDVLITWLIDYVEDTWGS DGNPITKTTSDYQDSDVSQEVRKYFCVKTMNP RGGGGSHHHHHHHHHH*HDEL* | 15<br><br><br><br>16 |
| pTEX-NB:A33RdN2:L10H | tctagaattattacatcaaaacaaaaaatggctcgctcgtttggagctaacag taccgttgtgttggcgatcatcttcttcggtgagtgattttccgatcttcttctcc gatttagatctcctctacattgttgcttaatctcagaaccttttttcgttgttcctg gatctgaatgtgtttgtttgcaatttcacgatcttaaaaggttagatctcgattg gtattgacgattggaatctttacgatttcaggatgtttatttgcgttgtcctctgc aggatccTCTACTCATAGAAAGGTTGCGTCTAGCA CTACACAATATGATCACAAAGAAAGCTGTAAT GGTTTATATTACCAGGGTTCTTGTTATATATTAC ATTCAGACTACCAGTTATTCTCGGATGCTAAAG CAAATTGCACTGCGGAATCATCAACACTACCC AATAAATCCGATGTCTTGATTACCTGGCTCATT GATTATGTTGAGGATACATGGGGATCTGATGGT AATCCAATTACAAAAACTACCGATTATCAA GATTCTGATGTATCACAAGAAGTTAGAAAGTA *TTTTTGTGTTAAAACAATGAAC*ccccgggggggga ggcagtcaccaccatcaccaccatcaccaccaccat*gatgagctc*tagct cgag *gssthrkvassttqydhkescnglyyqgscyilhsdyqlfsdakanctae sstlpnksdvlitwlidyvedtwgsdgnpitkttsdyqdsdvsqevrkyf cvktmnprggggshhhhhhhhhhhdel* | 17<br><br><br><br>18 |
| pTEX-NR:A33RdTM:L10H | tctagaattattacatcaaaacaaaaaatggcttcctctatgctctcttccgcta ctatggttgcctctccggctcaggccactatggtcgctcctttcaacggactt aagtcctccgctgccttcccagccacccgcaaggctaacaacgacactact tccatcacaagcaacggcggaagagttaactgcatgcaggtgtggcctcc gattggaaagaagaagtttgagactctctcttaccttcctgaccttaccggat ccATGATGACACCAGAAAACGACGAAGAGCAG ACATCTGTGTTCTCCGCTACTGTTTACGGAGA CAAAATTCAGGGAAAGAATAAACGCAAACGC GTGATTGGAGGAGGGGGTTCAGTGCGCCTAA ATCAATGCATGTCTGCTAACGAGGCTGCTATTA CTGACGCCGCTGTTGCCGTTGCTGCTGCATCA TCTACTCATAGAAAGGTTGCGTCTAGCACTAC ACAATATGATCACAAAGAAGCTGTAATGGTT TATATTACCAGGGTTCTTGTTATATATTACATTC AGACTACCAGTTATTCTCGGATGCTAAAGCAA ATTGCACTGCGGAATCATCAACACTACCCAAT AAATCCGATGTCTTGATTACCTGGCTCATTGAT TATGTTGAGGATACATGGGGATCTGATGGTAAT | 19 |

TABLE 1-continued

| Protein/Gene | Sequence | SEQ ID NO |
|---|---|---|
| | CCAATTACAAAAACTACATCCGATTATCAAGAT<br>TCTGATGTATCACAAGAAGTTAGAAAGTATTTT<br>TGTGTTAAAACAATGAACccccggggggggggaggcag<br>tcaccaccatcaccaccatcaccaccaccattagctcgag<br>massmlssatmvaspaqatmvapfnglkssaafpatrkanndttsitsn<br>ggrvncmqvwppigkkkfetlsylpdltgsmmtpendeeqtsvfsatv<br>ygdkiqgknkrkrviggggsvrlngcmsaneaaitdaavavaaassthr<br>kvassttqydhkescnglyyqgscyilhsdyqlfsdakanctaesstlpn<br>ksdvlitwlidyvedtwgsdgnpitkttsdyqdsdvsqevrkyfcvktm<br>nprgggshhhhhhhhhh | 20 |
| pTEX-A33RdTM:L10H | tctagaattattacatcaaaacaaaaaatgggatccATGATGACAC<br>CAGAAAACGACGAAGAGCAGACATCTGTGTT<br>CTCCGCTACTGTTTACGGAGACAAAATTCAGG<br>GAAAGAATAAACGCAAACGCGTGATTggaggagg<br>gggttcaGTGCGCCTAAATCAATGCATGTCTGCTA<br>ACGAGGCTGCTATTACTGACGCCGCTGTTGCC<br>GTTGCTGCTGCATCATCTACTCATAGAAAGGTT<br>GCGTCTAGCACTACACAATATGATCACAAAGA<br>AAGCTGTAATGGTTTATATTACCAGGGTTCTTG<br>TTATATATTACATTCAGACTACCAGTTATTCTCG<br>GATGCTAAAGCAAATTGCACTGCGGAATCATC<br>AACACTACCCAATAAATCCGATGTCTTGATTAC<br>CTGGCTCATTGATTATGTTGAGGATACATGGGG<br>ATCTGATGGTAATCCAATTACAAAAACTACATC<br>CGATTATCAAGATTCTGATGTATCACAAGAAGT<br>TAGAAAGTATTTTTGTGTTAAAACAATGAACcc<br>ccggggggggaggcagtcaccaccatcaccaccatcaccaccaccat<br>tagctcgag<br>mgsmmtpendeeqtsvfsatvygdkiqgknkrkrviggggsvrlnqc<br>msaneaaitdaavavaaassthrkvassttqydhkescnglyyqgscyil<br>hsdyqlfsdakanctaesstlpnksdvlitwlidyvedtwgsdgnpitktt<br>sdyqdsdvsqevrkyfcvktmnprgggshhhhhhhhhh | 21<br><br><br><br><br><br><br><br><br><br><br><br><br><br><br><br><br><br><br>22 |
| pTEX-NB:A33RdTM:aghFc | tctagaattattacatcaaaacaaaaaatggctcgtcgtttggagctaacag<br>taccgttgtgttggcgatcatcttcttcggtgagtgattttccgatcttcttctcc<br>gatttagatctcctctacattgttgcttaatctcagaacctttttttcgttgttcctg<br>gatctgaatgtgtttgtttgcaatttcacgatctaaaaggttagatctcgattg<br>gtattgacgattgtgaatctttacgatttcaggatgttatttgcgttgtcctctgca<br>ggatccATGATGACACCAGAAAACGACGAAGAG<br>CAGACATCTGTGTTCTCCGCTACTGTTTACGG<br>AGACAAAATTCAGGGAAAGAATAAACGCAAA<br>CGCGTGATTGGAGGAGGGGGTTCAGTGCGCC<br>TAAATCAATGCATGTCTGCTAACGAGGCTGCT<br>ATTACTGACGCCGCTGTTGCCGTTGCTGCTGC<br>ATCATCTACTCATAGAAAGGTTGCGTCTAGCA<br>CTACACAATATGATCACAAAGAAAGCTGTAAT<br>GGTTTATATTACCAGGGTTCTTGTTATATATTAC<br>ATTCAGACTACCAGTTATTCTCGGATGCTAAAG<br>CAAATTGCACTGCGGAATCATCAACACTACCC<br>AATAAATCCGATGTCTTGATTACCTGGCTCATT<br>GATTATGTTGAGGATACATGGGGATCTGATGGT<br>AATCCAATTACAAAAACTACATCCGATTATCAA<br>GATTCTGATGTATCACAAGAAGTTAGAAAGTA<br>TTTTTGTGTTAAAACAATGAACccccggggtccaccttt<br>gcccagctcctgaattgcttggaggtccttctgttttcttttttccacctaagcc<br>aaaagatacattgatgatttctaggacacctgaggttacttgcgttgttgttga<br>tgtttcacatgaagatccagaggttaagtttaattggtacgtttgatggagttga<br>agttcataatgctaagactaaaccaagggaagagcaatacgcctctacata<br>cagagttgtttcagttttgactgttcttcatcaagattggcttaacggaaagga<br>atacaagtgtaaagtttctaacaaggctttgccagctcctatcgaaaagaca<br>atttcaaaggctaaaggtcaaccaagggagcctcaagtttacactcttccac<br>catcaagagatgaattgacaaagaaccaagtttcattgacttgccttgttaag<br>ggattctacccttctgatattgctgttgaatgggagtcaaacggtcaaccaga<br>aaacaactacaagactacaccacctgttcttgattctgatggatctttcttctctt<br>actctaaacttactgttgataagtcaagatggcaacagggtaatgttttctctt<br>gttcagttatgcacgaggcacttcacaatcactacacacaaaaatctttatctt<br>tatccctggtaaataactcgag<br>gsmmtpendeeqtsvfsatvygdkiqgknkrkrviggggsvrlngcm<br>saneaaitdaavavaaassthrkvassttqydhkescnglyyqgscyilh<br>sdyqlfsdakanctaesstlpnksdvlitwlidyvedtwgsdgnpitktts<br>dyqdsdvsqevrkyfcvktmnprgppcpapellggpsvflfppkpkdt<br>lmisrtpevtcvvvdvshedpevkfnwyvdgvevhnaktkpreeqya<br>styrvvsvltvlhqdwlngkeykckvsnkalpapiektiskakgqprep | 23<br><br><br><br><br><br><br><br><br><br><br><br><br><br><br><br><br><br><br><br><br><br><br><br><br><br><br><br><br><br><br><br><br><br><br><br><br><br>24 |

TABLE 1-continued

| Protein/Gene | Sequence | SEQ ID NO |
|---|---|---|
| | qvytlppsrdeltknqvsltclvkgfypsdiavewesngqpennykttp pvldsdgsfflyskltvdksrwqqgnvfscsvmhealhnhytqkslsls pgk | |

*The underlined part is the sequence corresponding to vaccinia virus A33R.

EXAMPLE 1

Preparation of Recombinant Vector Expressing Vaccinia Virus A33R Antigen

A plant expression vector was prepared to express A33R of vaccinia virus in plants.

To this end, as shown in FIG. 1, a gene construct encoding A33R was synthesized by codon optimization for the tobacco plant *Nicotiana benthamiana* L. or *Nicotiana tabacum*.

A33R is a membrane protein, and in order to express it in soluble form, A33RdTM was designed by replacing the transmembrane domain (TMD) with GGGGS, which is a peptide linker. To accumulate the A33RdTM protein in the endoplasmic reticulum, the NB signal peptide was fused to the N-terminus of the protein, and the HDEL tetrapeptide, which is an endoplasmic reticulum retention signal peptide, was fused to the C-terminus. For protein purification, a His-tag containing 10 His repeats was fused to the C-terminus of the protein. To increase the binding efficiency between the protein and Ni-IDA resin, the peptide linker GGGGS was added between the protein and the His-tag.

The designed gene construct was inserted between the MacT promoter and RD29B terminator of the pTEX vector to prepare a plant expression vector.

EXAMPLE 2

Confirmation of Expression of A33R Antigen 2-1. Transient Expression of A33R Expression Vector The plant expression vector prepared in Example 1 was transformed into *Agrobacterium* GV3101 strain using electroporation. The transformed Agrobacteria were cultured with shaking in 5 mL of YEP liquid medium (10 g of yeast extract, 10 g of peptone, 5 g of NaCl, 50 mg/L of kanamycin, 25 mg/L of rifampicin) at 28° C. for 16 hours, and then 1 mL of primary culture was inoculated into 50 mL of new YEP medium and cultured with shaking at 28° C. for 6 hours. The Agrobacteria cultured in this way were collected by centrifugation (7,000 rpm, 4° C., 5 minutes), and then suspended in infiltration buffer [10 mM MES (pH 5.7), 10 mM MgCl2, 200 μM acetosyringone] so that the absorbance (O.D) value was 1.0 at a wavelength of 600 nm. Agroinfiltration was performed by injecting the Agrobacterial suspension into the back of *Nicotiana benthamiana* leaves using a syringe with the needle removed.

2-2. Confirmation of Expression of A33R Protein

After extracting the protein from the plant leaves prepared in Example 2-1 and centrifuging, the protein in the water-soluble fraction (Supernatant; S) and the protein in the pellet fraction (Pellet; P), and the fraction containing both the water-soluble fraction and the pellet (Total; T) were separated, respectively, and the expression of the recombinant A33R protein was confirmed by Western blotting.

More specifically, 10 μL of each fraction was mixed with SDS sample buffer and then heated. Then, each was electrophoresed on a 10% SDS-PAGE gel to confirm protein bands separated by size, and after moving it to a PVDF membrane, the blocking step was performed using 5% skim milk, and the antibodies that react with polyhistidine and the secondary antibodies that conjugated with HRP were sequentially conjugated, and the ECL solution was processed according to the method provided by the manufacturer to confirm the expression of the recombinant A33R protein.

As a result, as shown in FIG. 2, it was confirmed that the recombinant A33R antigen protein was expressed with high efficiency, and most of the expressed recombinant A33R protein was confirmed in the soluble fraction(S).

EXAMPLE 3

Isolation and Purification of A33R Antigen 3-1. Purification of Recombinant A33RdTM Protein 400 mL (50 mM Tris-HCl (pH 7.2), 300 mM NaCl, 70 mM imidazole, 0.5% Triton X-100, 100 mM sodium sulfite, 1.5% PVPP) of protein extraction solution was added to 200 g of *Nicotiana benthamiana* leaves expressing the recombinant A33RdTM protein, the tissues were crushed with a blender, and the protein extract was recovered by centrifugation at 12,000×g for 40 minutes at 4° C. To remove impurities including other proteins in the plant, acetic acid was added to the extract liquid to adjust the pH to 5.0, and centrifuged at 12,000×g at 4° C. for 10 minutes to remove impurities. The acidic extract liquid was neutralized (pH 7.4) with NaOH, centrifuged at 12,000×g at 4° C. for 10 minutes, and finally passed through a 0.22 μm filter to remove impurities.

To isolate and purify the recombinant A33RdTM protein from the protein extract liquid, affinity chromatography was performed using a column filled with Ni-NTA agarose resin. After mounting the column filled with 25 mL of the resin on the FPLC, 250 mL of washing solution 2 (50 mM Tris-HCl (pH 7.2), 300 mM NaCl, 70 mM imidazole) was flowed through to equilibrate, the recovered protein extract liquid was passed through the column to adsorb the protein onto the resin, and then 500 mL each of washing solution 1 (50 mM Tris-HCl (pH 7.2), 300 mM NaCl, 70 mM imidazole, 0.5% Triton X-100) and washing solution 2 were sequentially flowed to wash the resin, and 100 mL each of elution solution 1 (50 mM Tris-HCl (pH 7.2), 300 mM NaCl, 100 mM imidazole) and elution solution 2 (50 mM Tris-HCl (pH 7.2), 300 mM NaCl, 300 mM imidazole) were sequentially flowed to elute the recombinant A33RdTM protein from the resin. All processes were carried out based on the absorbance graph at 280 nm of the FPLC equipment. The elution solution containing the recombinant A33RdTM protein was buffer replaced and concentrated to the final solution (50 mM Tris-HCl (pH 7.2), 300 mM NaCl) using a 10 kDa size filter. The isolated and purified recombinant A33RdTM protein was confirmed through electrophoresis (SDS-PAGE) and then Coomassie staining.

Figure 3:
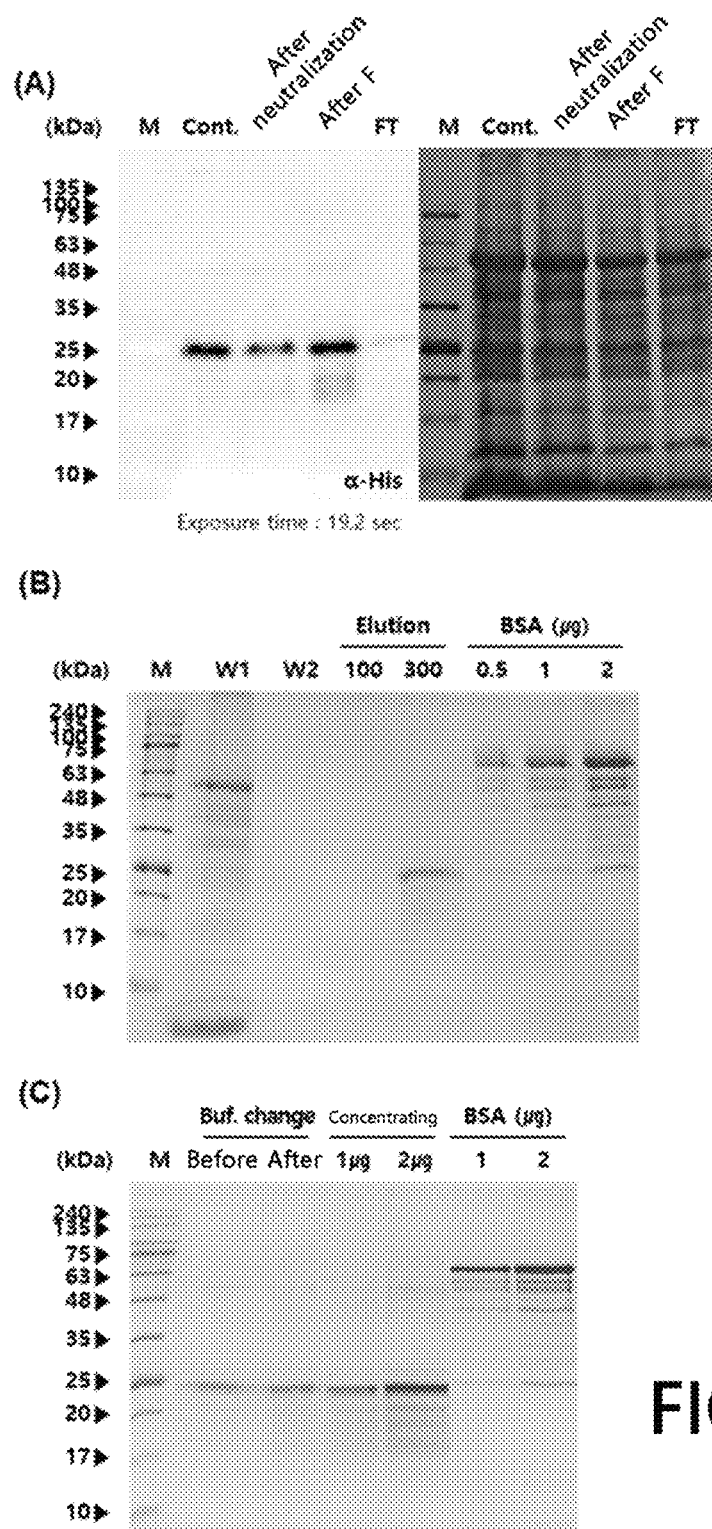
FIG. 3 shows the results of electrophoresis of a protein sample obtained during the process of isolating and purifying the A33R protein (A33RdTM) and then confirmed by Western blot or Coomassie blue staining.

As a result, 2.79 mg of A33RdTM protein was obtained with a yield of 13.8 mg/kg [concentration (nanodrop standard): 0.4 mg/ml], and as shown in FIG. 3, it was confirmed that the recombinant A33RdTM protein was purified to a high level of purity.

EXAMPLE 4

Preparation of Recombinant Vector Expressing Various Types of Vaccinia Virus A33R Antigen From the gene construct prepared in Example 1, (A) a second gene construct replacing A33RdTM with the C-terminus of the TMD of the A33R protein (N-terminus deletion; positions 58-185 in the amino acid sequence of SEQ ID NO: 1); (B) a third gene construct replacing A33RdTM with the C-terminus of the TMD of the A33R protein (additional N-terminal deletion; positions 82-185 in the amino acid sequence of SEQ ID NO: 1); (C) a fourth gene construct prepared to target the protein to the chloroplast instead of the endoplasmic reticulum; (D) a fifth gene construct designed to target the protein to the cytosol instead of the endoplasmic reticulum; and (E) a sixth gene construct in which the peptide linker and His-tag were replaced with human IgG Fc fusion (non-glycosylation) were produced as shown in FIG. 4, and protein expression was confirmed in the same manner as in Example 2.

Figure 10:
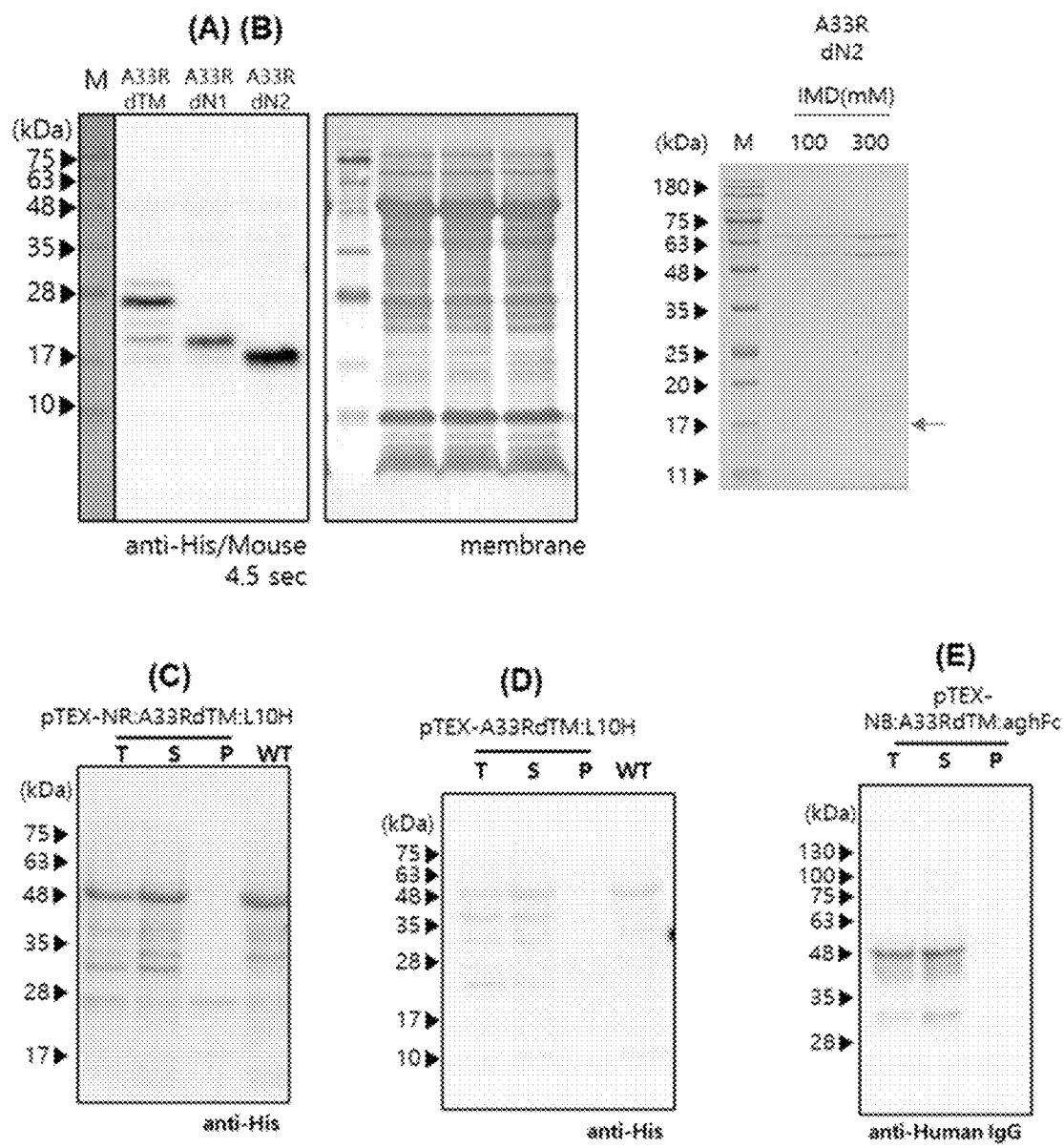
FIG. 10 is a picture of a band obtained by performing Western blot to confirm the expression of the vaccinia virus A33R antigen of each gene construct in FIG. 4 (T, Total extract; S, Soluble; P, Pellet).

As a result, as shown in FIG. 10, in the case of A33RdN2, the purity after purification was low, and other than that, it was confirmed that protein expression was lower than A33RdTM.

EXAMPLE 5

Antibody Testing Following Second-Generation Smallpox Vaccination

The recombinant A33RdTM protein isolated and purified in Example 3 was each dispensed into a plate (Nunc-Immuno Plates; Thermo Scientific, UK) at 50 ng per well, reacted at 4° C. for 16 hours or more, washed with a wash buffer (0.05% Tween 20 dissolved in PBS), and then a blocking buffer (1% BSA dissolved in PBS) was dispensed at 200 μl per well, and reacted at 37° C. for 2 hours to alleviate non-specific binding.

Subsequently, it was washed with a washing buffer, and the serum of a second-generation smallpox vaccine recipient was binary diluted from 1:10 in dilution buffer (0.1% BSA dissolved in PBS) and dispensed into the wells. It was reacted at 37° C. for 2 hours, washed with a washing buffer to remove serum samples, and then 100 μl of HRP-conjugated goat anti-human IgG-F (ab') 2 fragment-specific antibody (Jackson ImmunoResearch Laboratories INC, USA) diluted at 1:10,000 was dispensed each and reacted at room temperature for 30 minutes. It was washed with a wash buffer, developed with TMB (BioLegend, USA) solution, and absorbance was measured at 450 nm.

To test antibodies in recipients of the second-generation smallpox vaccine, antibodies recognizing the recombinant A33RdTM protein were measured using a self-constructed indirect ELISA method. As a result of measuring antibodies against vaccinia virus in serum isolated 3 weeks after vaccination with the second generation smallpox vaccine, as shown in FIG. 11, it was confirmed that the binding antibodies was higher compared to the negative control group (serum isolated before vaccination).

What is claimed is:

1. A gene construct, comprising a polynucleotide encoding a vaccinia virus recombinant A33R protein comprising the amino acid sequence of SEQ ID NO: 2.

2. The gene construct of claim 1, further comprising a polynucleotide encoding an endoplasmic reticulum (ER) signal peptide and/or a polynucleotide encoding an endoplasmic reticulum (ER) retention signal peptide, wherein the polynucleotide encoding the endoplasmic reticulum signal peptide comprises the nucleotide sequence of SEQ ID NO: 5 encoding new chaperone binding protein, and the endoplasmic reticulum retention signal peptide comprises an amino acid sequence selected from HDEL (His-Asp-Glu-Leu) (SEQ ID NO: 6), HEEL (His-Glu-Glu-Leu) (SEQ ID NO: 7), KDEL (Lys-Asp-Glu-Leu) (SEQ ID NO: 8), KEEL (Lys-Glu-Glu-Leu) (SEQ ID NO: 9), RDEL (Arg-Asp-Glu-Leu) (SEQ ID NO: 10) or REEL (Arg-Glu-Glu-Leu) (SEQ ID NO: 11).

3. The gene construct of claim 2, further comprising a polynucleotide encoding a His-tag and/or a polynucleotide encoding a peptide linker, wherein the peptide linker is (GGGGS) n (SEQ ID NO: 4), where n is an integer from 1 to 5.

4. The gene construct of claim 3, wherein the following (i) to (v) are linked sequentially:
  (i) the polynucleotide encoding an endoplasmic reticulum signal peptide,
  (ii) the polynucleotide encoding the recombinant A33R protein,
  (iii) the polynucleotide encoding the peptide linker,
  (iv) the polynucleotide encoding a His-tag, and
  (v) the polynucleotide encoding an endoplasmic reticulum (ER) retention signal peptide.

5. The gene construct of claim 4, wherein the gene construct comprises the nucleotide sequence of SEQ ID NO: 13.

6. A recombinant vector comprising the gene construct of claim 1.

7. A transgenic organism except humans, transformed with the recombinant vector of claim 6.

8. The transgenic organism except humans, according to claim 7, wherein the transgenic organism is a plant.

9. A method for producing a vaccinia virus recombinant antigen protein, comprising the following (a) and (b):
  (a) transforming the recombinant vector of claim 6 into a plant; and
  (b) isolating and purifying a vaccinia virus recombinant A33R protein from the plant.

10. The method for producing a vaccinia virus recombinant antigen protein of claim 9, wherein the vaccinia virus recombinant A33R protein is expressed in a soluble form in the plant.

11. A vaccinia virus recombinant antigen protein comprising the amino acid sequence of SEQ ID NO: 2.

12. A vaccinia virus recombinant antigen protein produced using the recombinant vector of claim 6, comprising the amino acid sequence of SEQ ID NO: 2.

13. A composition for diagnosing antibodies against orthopoxvirus comprising the vaccinia virus recombinant antigen protein of claim 11, wherein the orthopoxvirus is smallpox virus, vaccinia virus, cowpox virus, or monkeypox virus.

14. A kit for diagnosing antibodies against orthopoxvirus, comprising the vaccinia virus recombinant antigen protein of claim 11, wherein the orthopoxvirus is smallpox virus, vaccinia virus, or monkeypox virus.

15. The kit for diagnosing antibodies against orthopoxvirus of claim 14, further comprising a chromogenic enzyme, a radioisotope, a chromophore, a luminescent substance, or a fluorescent substance.

16. A method of diagnosing antibodies against orthopoxvirus, comprising the following steps:
   (a) contacting a biological sample isolated from an individual with the vaccinia virus recombinant A33R protein comprising the amino acid sequence of SEQ ID NO: 2; and
   (b) confirming whether the vaccinia virus recombinant A33R protein binds to specific antibodies against orthopoxvirus in the biological sample through an antigen-antibody reaction, wherein the orthopoxvirus is smallpox virus, vaccinia virus, or monkeypox virus.

* * * * *